United States Patent [19]

Yen

[11] Patent Number: 5,725,804
[45] Date of Patent: Mar. 10, 1998

[54] NON-CROSSLINKED PROTEIN PARTICLES FOR THERAPEUTIC AND DIAGNOSTIC USE

[75] Inventor: Richard C. K. Yen, Yorba Linda, Calif.

[73] Assignee: Hemosphere, Inc., Irvine, Calif.

[21] Appl. No.: 471,650

[22] Filed: Jun. 6, 1995

Related U.S. Application Data

[63] Continuation-in-part of Ser. No. 212,546, Mar. 14, 1994, Pat. No. 5,616,311, which is a continuation-in-part of Ser. No. 69,831, Jun. 1, 1993, abandoned, and Ser. No. 959,560, Oct. 13, 1992, Pat. No. 5,308,620, which is a continuation-in-part of Ser. No. 641,720, Jan. 15, 1991, abandoned.

[51] Int. Cl.$^6$ ............... A61K 9/64; A61K 47/42; B01J 13/00
[52] U.S. Cl. ............... 252/314; 252/311; 424/484; 424/491; 514/776; 514/937; 514/965
[58] Field of Search ............... 264/4.3; 427/213.3, 427/213.33, 2.14, 2.21; 514/965, 937, 776; 252/311, 314; 424/491

[56] References Cited

U.S. PATENT DOCUMENTS

| | | | |
|---|---|---|---|
| 3,565,559 | 2/1971 | Sato et al. | 428/402.2 X |
| 4,147,767 | 4/1979 | Yapel, Jr. | 424/499 |
| 4,325,937 | 4/1982 | Spence et al. | 424/493 |
| 4,410,507 | 10/1983 | Chia et al. | 252/311 X |
| 4,818,542 | 4/1989 | DeLuca et al. | 424/491 |
| 4,822,535 | 4/1989 | Ekman et al. | 264/4.3 |
| 4,921,705 | 5/1990 | Arai et al. | 424/450 |
| 4,963,367 | 10/1990 | Ecanow | 424/484 X |
| 5,069,936 | 12/1991 | Yen | 427/213.33 |
| 5,104,674 | 4/1992 | Chen et al. | 426/573 |
| 5,149,540 | 9/1992 | Kunihiro et al. | 424/489 |
| 5,308,620 | 5/1994 | Yen | 424/484 |
| 5,374,441 | 12/1994 | Gibson et al. | 426/656 |

*Primary Examiner*—Richard D. Lovering
*Attorney, Agent, or Firm*—Townsend & Townsend & Crew

[57] ABSTRACT

Albumin particles in the nanometer and micrometer size range in an aqueous suspension are rendered stable against resolubilization without the aid of a crosslinking agent and without denaturation, by the incorporation of a stabilizing agent in the particle composition. Particles which are primarily albumin in the nanometer and micrometer size range in an aqueous suspension are rendered stable against resolublization by the incorporation of a reducing agent, oxidizing agent, hydrogen-accepting molecule, high molecular weight polymer, sulfur-containing ring compound or combinations thereof.

11 Claims, No Drawings

NON-CROSSLINKED PROTEIN PARTICLES FOR THERAPEUTIC AND DIAGNOSTIC USE

CROSS REFERENCE TO RELATED APPLICATIONS

This application is a continuation-in-part of application Ser. No. 08/212,546, filed Mar. 14, 1994 and now U.S. Pat. No. 5,616,311; which is a continuation-in-part of application Ser. No. 08/069,831, filed Jun. 1, 1993 and now abandoned, and Ser. No. 07/959,560, filed Oct. 13, 1992 and now U.S. Pat. No. 5,308,620, which is a continuation-in-part of application Ser. No. 07/641,720 filed Jan. 15, 1991, now abandoned.

BACKGROUND OF THE INVENTION

Therapeutic drugs are typically administered orally or by intramuscular, subcutaneous, intraperitoneal, or intravenous injections. Intravenous injection is the most direct means of administration and results in the fastest equilibration of the drug with the blood stream. Drugs injected intravascularly reach peak serum levels within a short time, however. Toxic effects can result from such high serum levels, especially if the drug is given as a bolus injection. To avoid such high concentrations, drugs can be administered slowly as a continuous drip. This however requires prolonged nursing care and, in some cases, hospitalization which itself entails high cost. To avoid this, efforts have been made to develop means of administering drugs within stable carriers which allow bolus intravenous injections but provide a gradual release of the drugs inside the vasculature.

The reticuloendothelial system (RES) directs drugs preferentially to the liver and spleen, and its uptake of a carrier thus interferes with the distribution of the drug to other parts of the body. If however the carriers are small enough so that the phagocytic cells such as macrophages do not preferentially ingest them, the carriers would escape the RES long enough to perform other tasks. If the carriers also contain antibodies or other ligands on their surfaces which specifically bind to antigenic sites or specific receptors, these antibodies or ligands will direct the drugs to specific cell types containing these sites or receptors. This would result in a higher concentration of the drug near the surfaces of the targeted cells without a higher risk of systemic side effects.

Entrapment of useful agents serves useful purposes in other medical applications as well. Tiny air bubbles, for example, are useful in ultrasonography, where they are used to provide strong contrast to blood vessels and organs traversed by the bubbles. If the bubbles are injected through a peripheral vein, however, they must travel through the right heart, the pulmonary vasculature and then the left heart before they can reach to the other internal organs. Since the bubbles are inherently unstable, they are not able to remain small enough for effective ultrasonographic contrast by the time the intended organs are reached. Entrapment of small air bubbles in small particulate carriers would allow the bubbles to serve their intended function even after long distances of travel within the intravascular compartment.

Similar advantages by using small particulate carriers for contrast material for CAT scans and nuclear magnetic resonance (NMR) scans. Abnormally high concentrations of contrast material at an injection site which might lead to false interpretation of the results could be avoided by administration of the contrast material as an agent retained in a particulate carrier to be released later at the site of the organ of interest.

Oxygen is another vital biological molecule that can be carried within a particulate carrier if the carrier contains hemoglobin. While hemoglobin molecules in large amounts are toxic to the human body, entrapment of hemoglobin within a particulate carrier will reduce its toxicity to vital organs while permitting it to deliver oxygen.

To summarize, stable porous and membraneless carriers which deliver biological agents to sites within the body offer many advantages. The two major approaches of particulate carriers in the prior art are liposomes and microspheres.

In liposomes, a shell is formed by a lipid layer or multiple lipid layers surrounding a central hydrophilic solution containing the medication. The lipid layers are inherently unstable and much research went into stabilizing them during the manufacturing process. In addition, the lipid layer(s) may serve as a barrier to diffusion of certain molecules. It is difficult for a hydrophilic substrate to diffuse through the hydrophobic layers into the interior of the liposomes, or conversely, for the drugs to be released without physical destruction of the lipid layer(s).

Microspheres, in contrast to liposomes, do not have a surface membrane or a special outer layer to maintain their intactness. Most microspheres are more or less homogenous in structure. To maintain the stability of the microspheres, manufacturing procedures in the prior art include a cross-linking process to stabilize the microspheric mass. The cross-linking agent however alters the chemical nature of the natural biological molecule, which may render the resultant product antigenic to the injected host. An anaphylactic reaction to such a newly created antigenicity is unpredictable and potentially dangerous.

Protein particles in essentially spheric form are useful in the encapsulation and delivery of nutrients and biologics such as oxygen, enzymes, drugs, and information molecules (DNA, RNA and hybrid molecules of DNA and RNA) to cells and tissues.

To preserve the intactness of the spheres after synthesis and to allow further purification or concentration of the spheres, a variety of methods have been used during or after synthesis to prevent resolubilization of the protein particles. These methods include heat denaturization (see, Evans, et al. U.S. Pat. No. 3,663,685 and Widder, et al., *Adv. Pharmacol. and Chemother.* 16:213–271 (1979)); addition of a cross-linking agent to initiate find complete formation of particles composed of covalently and irreversibly crosslinked protein molecules (see Oppenheim, U.S. Pat. No. 4,107,288); and the addition of a cross-linking agent following the formation of protein spheres in the presence of alcohol (see Yen, U.S. Pat. No. 5,069,936). More recently, a method has been described for stabilizing protein spheres against resolubilization by incorporating hemoglobin molecules into albumin spheres (see Yen, co-pending application Ser. No. 08/212,546.

Other literature of potential relevance to the present invention is as follows.

U.S. Pat. No. 4,269,821, Kreuter, et at., May 26, 1981, for "Biological Material" discloses processes for the preparation of submicroscopic particles of a physiologically acceptable polymer associated with a biologically active material by using a cross-linking agent such as a polymerisable material soluble in a liquid medium (methyl methacrylate as an example).

U.S. Pat. No. 3,663,685, Evans et al., May 16, 1972, for "Biodegradable Radioactive Particles" (hereafter "Evans") discloses a method of preparing biodegradable radioactive particles by using heated water-oil solutions.

Widder, et al., "Magnetically Responsive Microspheres And Other Carriers For The Biophysical Targeting Of Antitumor Agents", *Advances in Pharmacology and Chemotherapy* 16:213–271 (1979) disclose emulsion polymerization methods of preparation of albumin microspheres (pages 233–235) and preparation of magnetically responsive albumin microsphere (pages 241–250). The methods essentially involve emulsification and heat denaturation of a water-oil solution to produce and stabilize microspheres. The authors also state that for heat sensitive drugs the microspheres are stabilized by chemical cross-linking.

To summarize this literature, typical prior art processes require irradiation, heat, or reaction with a cross-linking agent to polymerize the "monomers" (which are the individual protein molecules such as human serum albumin or gelatin molecules) to convert them to stable particles. Prior art methods which use heat to cross-link and stabilize the protein involve irreversible denaturation of the proteins which renders them "foreign" to the host body.

U.S. Pat. No. 5,049,322, Devissaguet, et al., Sep. 17, 1991 discloses a method of producing a colloidal system containing 150–450 nm particles by dissolving a protein ingredient in a solvent and adding ethanol or mixture of ethanol containing surfactant. Devissaguet does not disclose adding a second protein ingredient. Devissaguet discloses a process of producing colloidal spheres which have a distinct "wall" (column 2, line 25) or "layer" (column 8, line 33) of substance A which is different from the "core" of substance B (column 8, line 18), where the substance B may be a biologically active substance. This disclosure requires that the wall material and the core material both be present in a first liquid phase, which is then added to a second liquid phase that is a non-solvent for both materials. The resulting product is not homogeneous, and relies on the wall for its particle integrity.

Albert L. Lehninger, *Biochemistry: The Molecular Basis of Cell Structure and Function* (1972) discloses that ethanol as a solvent can decrease the ionization of proteins and therefore promote their coalescence and produce "colloidal suspensions". Lehninger does not disclose a special method of preparing colloidal suspensions, but rather generally a method of promoting protein coalescence by using ethanol, "[s]ince a decrease in dielectric constant increases the attractive force between two opposite charges, ethanol decreases the ionization of proteins and thus promotes their coalescence" (page 134, lines 21 through 25, citations omitted). Lehninger has defined the process of "coalescence" as a process leading to "insoluble aggregates" (page 133, lines 31 through 35).

"Remington's Pharmaceutical Sciences", 7th ed. (1985) discloses some general knowledge of "colloidal dispersions". Remington teaches that adding surfactant "stabilizes the dispersion against coagulation" (page 286, column 2, lines 59 and 60), where the surfactant molecules "arrange themselves at the interface between water and an organic solid or liquid of low polarity in such a way that the hydrocarbon chain is in contact with the surface of the solid particle or sticks inside the oil droplet while the polar bead group is oriented towards the water phase" (page 286, column 2, lines 30 through 35). Remington does not specially disclose the use of any particular protein molecules such as globin as the primary protein.

SUMMARY OF THE INVENTION

It has now been discovered that protein particles in the nanometer and micrometer size range, suspended in an aqueous medium, can be made stable against resolubilization (i.e., prevented from redissolving) upon storage, dilution and dialysis, by the inclusion of certain noncrosslinking additives, and that noncrosslinking additives can also reduce or eliminate the tendency of protein particles to aggregate in aqueous suspensions. In particular, particles of non-crosslinked and non-denatured albumin in a suspension are stabilized against resolubilization by the inclusion of reducing agents, oxidizing agents, phosphorylated compounds, sulfur containing compounds, polymers and combinations thereof.

A convenient method of forming the particles of either protein is by adding a water-soluble lower alkyl alcohol to an aqueous solution of the protein. Upon formation of the particles, the solution turns turbid. The stabilizing agent may then be added in a volume sufficiently small so that the aqueous solvent medium (for the agent) will not cause a decrease in the alcohol concentration that will disrupt the protein particles. After a minimal time of interaction which allows the stabilizing agent to completely stabilize the protein spheres against resolubilization, the suspension may be diluted in an alcohol-free aqueous medium to lower the alcohol content. Alternatively, the suspension may be dialyzed against an aqueous medium to remove any molecular species small enough to pass through the dialysis membrane (i.e. alcohol, surfactant, and other added but unincorporated reagents) or washed by repeated cycles of centrifugation and resuspension of the pelleted protein particles in a new medium. Even if neither dilution or dialysis is performed and the particle suspension is administered as formed, a similar effect occurs when the suspension is administered to a patient where it combines with the patient's serum or other bodily fluids. In any case, both dilution and dialysis raise the tendency of the particles to return to solution. In a laboratory vessel, resolubilization is evident when the turbidity disappears and is replaced once again by a clear solution. The additive prevents this from happening without the need for crosslinking. The benefits of the particulate form are thus retained without the need for a crosslinking reaction or the danger of an irreversibly crosslinked particle.

Aggregation of the particles arises in some cases immediately upon their formation and, in some cases, upon dialysis or storage for several hours. Aggregated particles are often too large to be administered effectively, and when close control of the particle size is desired, this is defeated by aggregation. The discovery that aggregation can be avoided by the inclusion of the additives listed above therefore adds a further benefit to the benefits achieved by the elimination of crosslinking.

This invention therefore permits the formation of albumin particles in the nanometer to micrometer size range, in a form closer to their natural form than the forms of the prior art. The particles thus constitute a more closely controlled agent for in vivo administration, either for their own administration or as a vehicle for other therapeutic or diagnostic agents, or as a building block for cellular processes. These and other features and advantages of the invention will be apparent from the description which follows.

DETAILED DESCRIPTION OF THE INVENTION AND PREFERRED EMBODIMENTS

The protein particles which are the subject of this invention are monodisperse particles, generally spherical in shape. The term "monodisperse" as used herein denotes discrete single particles which are individually suspended in the aqueous suspension and are neither attached nor adhered to other particles, as distinct from aggregates or aggregated particles, which are groups of two or more, and as many as a hundred or more, such particles adhering to each other by surface interaction or attraction, the aggregates themselves being suspended in the medium in the same manner as the monodisperse particles. While large aggregates can be discerned by the naked eye, a microscope is generally required to differentiate mid-size to small aggregates from monodisperse particles.

Agents which were found to have a stabilizing effect on protein particles include reducing agents, oxidizing agents, high molecular weight polymers (i.e. polyethylene glycol), hydrogen acceptor molecules (i.e. NADP), carboxylic acids having multiple oxygen functionality, and sulfur containing ring compounds (i.e. thioctic acid).

More particularly, the stabilizing agents which are reducing agents can be either organic reducing agents such as dithiothreitol or mercaptoethanol, or inorganic reducing agents such as sodium sulfite or sodium bisulfite.

Stabilizing agents which are high molecular weight polymers will typically be polyethyleneglycols.

An example of a stabilizing agent which is a hydrogen acceptor molecule is NADP.

Yet another group of stabilizing agents are those which can be classified as sulfur containing ring compounds, an example of which is thioctic acid.

Still yet another group of stabilizing agents are those which have multiple oxygen functionality, particularly alpha-keto carboxylic acids, alpha-hydroxy carboxylic acids and dicarboxylic acids. Examples in this group include lactic acid (D and L forms), succinic acid, ascorbic acid and 1-ketoglutaric acid.

The stabilizing agents can either be present in the protein solution before the addition of alcohol, such that particles subsequently formed are stable against resolubilization, or be added to suspensions of protein particles. Similarly, biological molecules can be added to the protein solution before formation of the particles or spheres, or they can be added after the appearance of turbidity which indicates the formation of particulates. The biological molecules are carried either in the interior or on the surface of the spheres, or both. Additionally, the properties of such added molecules are not altered by the stabilizing agents.

The size range of the particles of the present invention extends into both nanometer and micrometer ranges. In general, particles of interest will primarily range from about 50 to about 5000 nanometers in diameter, in monodisperse form. The appropriate or optimal size range for particular uses of the particles or methods of administration will vary with the use or method.

The aqueous medium in which the particles are formed is a homogeneous, water-containing liquid, which may also contain additional components such as surface active agents, buffering agents and inorganic ions. Aqueous media of particular interest in the context of this invention are distilled or deionized water, normal saline and hypotonic saline. In preferred embodiments of the invention, the aqueous medium in which the particles are formed further includes the alcohol which induces the turbidity, the alcohol being fully miscible with the water in the medium to result in a homogeneous continuous phase. In most applications of the invention, the particles will constitute at least about 1.0 g per liter of the suspension, preferably from about 1.0 g per liter to about 150 g per liter, and in many applications at least about 3.0 g per liter, and preferably from about 5.0 g per liter to about 50 g per liter.

In embodiments of the invention in which the suspension is subjected to dilution in, or dialysis against, a second aqueous medium, the second aqueous medium will also be a water-containing liquid, most likely containing neither alcohol nor surfactants. The second aqueous medium is alcohol-free, and is preferably a biological fluid, a fluid similar in composition to a biological fluid, or a fluid which is compatible with a biological fluid. Compatible fluids are those which do not cause adverse physiological effects upon administration. Examples are water, normal saline, and 5% aqueous human serum albumin (HSA).

Dilution may be done to varying degrees, although in most cases the amount of aqueous medium added will result in a volume increase of at least about 50%. The invention is particularly effective when dilutions are performed by adding an equal volume of aqueous medium (100% volume increase) or greater.

The alcohol referred to above is a lower alkyl alcohol, preferably either methanol, ethanol, n-propanol, isopropanol or n-butanol. Among these alcohols, ethanol and n-butanol are particularly preferred. When included, the alcohol is present in an amount sufficient to induce turbidity in the initial aqueous solution of the protein, and preferably to cause precipitation of all protein dissolved in the solution. In most applications, this mount will fall within the range of about 5% to about 80% by volume of the aqueous medium, and preferably from about 10% to about 50%.

The primary protein component of the particles of interest in the present invention is albumin, which is neither denatured nor crosslinked. The albumin, the albumin may be any of the various known types of albumin, the choice being governed by the route or method of administration to the patient. Serum albumin, particularly human serum albumin, is preferred.

The surfactants used in certain embodiments of the invention are anionic water-soluble surfactants, preferably sodium or potassium alcohol sulfates. Particularly preferred are sodium or potassium $C_6$–$C_{16}$ alkyl sulfates and sodium or potassium $C_8$–$C_{14}$ alkyl sulfates. Sodium lauryl sulfate and sodium tetradecylsulfate are the most preferred.

The amount of surfactant used in these embodiments may vary depending on the other system parameters. For albumin-based particles where the particles are formed as a suspension in a first aqueous medium, then diluted by addition of a second aqueous medium, best results will be obtained using at least about 1.0 g of surfactant per liter of the suspension prior to dilution or dialysis. Preferably, the surfactant constitutes from about 0.5 g to about 5 g per liter of the suspension, particularly when the suspension contains at least about 15 g of particles per liter of suspension.

The following examples are offered solely for purposes of illustration, and are intended neither to limit nor to define the invention.

EXAMPLE 1

This example illustrates the synthesis of particles of human serum albumin (HSA), followed by dilution in either water or normal saline, the particles being formed without the inclusion of a stabilizing agent against resolubilization upon dilution, but with the use of sodium lauryl sulfate (SLS) to prevent aggregation of the particles.

The HSA was prepared by diluting stock HSA (25% in normal saline) in distilled water to 80 mg/mL. Mixtures of this solution were then prepared by combining it with water and SLS in the amounts shown in Table I, followed by the addition of ethanol. As shown in the table, turbidity resulted in each tube, with the particles in tubes 30 and 31 (containing 2 mg/mL and 1 mg/mL, respectively, of the SLS based on the solution prior to the addition of the ethanol) being monodisperse and those in tube 32 (lacking SLS) being aggregated. The table also shows that upon dilution of the tubes with equal volumes of distilled water or normal saline buffer, the contents of tubes 30 and 31 redissolved into a clear solution within one hour.

These results indicate that a stabilizing agent is needed for HSA particles to prevent redissolving of the particles upon dilution, and a surfactant is needed to prevent the particles from aggregating.

TABLE I

HSA Particles with Surfactant but no Stabilizing Agent

Tube Contents (balance: water to achieve total volume of 1.0 mL before addition of alcohol) Size (and Condition) of

| Tube No. | HSA (mL at 80 mg/mL) | SLS (mL at 8 mg/mL) | Ethanol (mL) | Particles Formed (μm) | Effect of Dilution |
|---|---|---|---|---|---|
| 30 | 0.25 | 0.250 | 0.8 | 0.1 (monodisperse) | redissolves |
| 31 | 0.25 | 0.125 | 0.8 | 0.05 (monodisperse) | redissolves |
| 32 | 0.25 | 0.000 | 0.8 | (aggregated) | — |

EXAMPLE 2

This example illustrates the use of a stabilizing agent to prevent resolubilization of human serum albumin (HSA) spheres.

Ethanol (70% in water) was added dropwise to a solution of HSA (150 mg/mL in normal saline, N.S.) in a volume of from about 1.2 to 1.8 times the volume of protein solution, to form a turbid suspension of spheres. The average diameter of the spheres examined under light microscopy was about 0.8 to 1.2 microns. When the HSA concentration is 50 mg/mL or lower, the spheres or particles formed are typically 0.2 to 0.5 microns in diameter.

Aliquots of the suspension were dispensed into tubes (0.5 mL per robe). A stock solution of stabilizing agent such as a reducing agent (1M of sodium bisulfite) was serially diluted two fold each step for 12 steps. Then 5 μL of the stabilizing agent at various concentrations was added to 0.5 mL of unstabilized sphere suspensions. Five microliters of N.S. was added to each of the control tubes. The protein particles remain intact at this level of dilution (typically 1% dilution). Larger volumes of any non-alcohol containing aqueous media (e.g. greater than 2 volumes per 100 volumes of nonstabilized protein particle suspensions) will increase the risk of partial resolubilization of the protein particles, resulting in a lower concentration of particles which had approximately the same size range.

After 2 hours, an aliquot from each tube was examined under the microscope to check for any change in the average diameter of the spheres or the presence of aggregates. None were observed.

After incubation for at least 2 hours, normal saline (1.5 mL) was added to each tube. Control tubes and HSA particle suspensions with insufficient amount of stabilizing agent turned from turbid suspensions to clear solutions within 5 minutes. The minimum final concentration of stabilizing agents (before addition of the non-alcohol dilution medium) needed to maintain turbidity after dilution of the alcohol content was noted. The highest final concentration of stabilizing agents (before addition of the non-alcohol dilution medium) which allow the particles to remain monodisperse without the formation of aggregates was also noted.

After the approximate effective concentrations (the range between the maximal and minimal final concentrations) from the twofold dilutions of stock stabilizing agents were found, the experiments were repeated with narrower ranges of final concentrations to further refine the effective range accurately.

Additional agents were checked for their ability to stabilize HSA spheres against resolubilization. The effect of a longer incubation times (up to 18 hr) was also examined. It was found that longer incubation times allowed a lower concentration of stabilizing agent to be used while retaining effectiveness in preventing resolubilization of the spheres, without aggregate formation.

Table II provides the minimal and maximal final concentrations of each stabilizing agent in the final volume of sphere suspension (before addition of the non-alcohol dilution medium) that was needed to maintain particulate intactness against resolubilization without causing aggregate formation.

TABLE II

Effective Concentrations of Agents Used to Stabilize Protein Spheres

| Agent | Effective Concentrations (μM) | |
|---|---|---|
| | Minimum | Maximum |
| Sodium Bisulfite* (NaHSO$_3$) | 650 | 5000 |
| Sodium Sulfide* | 500 | 2500 |
| NADP* | 250 | 2500 |
| DTT* | 100 | 1000 |
| Glutathione* (reduced form) | 100 | 2500*** |
| PEG (MW 2000)* | 12.5 | 2500 μg/mL |
| PEG (MW 5000)* | 12.5 | 2500 μg/mL |
| PEG (MW 8000)* | 12.5 | 2500 μg/mL |
| Sodium Bisulfite | 50 | 500 |
| Sodium Sulfite (Na$_2$SO$_3$) | 50 | 1000 |
| 2-Mercaptoethanol | 10** | 5000 |
| DL-Lactic Acid | 500 | 1000 |
| Thioctic Acid (oxidized) | 10 | 500 |
| Stannous Chloride | 250 | 2500 |
| Succinic Acid (4*) | 1000 | 2500 |
| Ascorbic Acid (4*) | 1000 | 2500 |
| 1-Ketoglutaric Acid (4*) | 500 | 1000 |
| Cysteine (4*) | 500 | 2500 |
| Manganese Chloride (4*) | 1000 | 2500 |

*Incubation time between agent and sphere suspension was 2 hours, all other incubation times were approximately 18 hours.
**Lowest final concentration tested was 10 μM.
***Highest final concentration tested was 2500 μM.
4* Initial conc of HSA was 5%, instead of 15% which required approximately double the minimum concentration of agent to achieve stability against resolubilization.

EXAMPLE 3

This example illustrates particular agents that were not effective in protecting spheres against resolubilization.

The same experimental protocol was followed as described in Example 2. Turbidity of the suspensions was reversed to clear solutions within 2 hours of dilution with normal saline (3 volumes per volume of suspension.) Table III provides the unsuccessful agents used.

TABLE III

Ineffective Stabilizing Agents

| Agent | Final concentration checked (μM, unless specified) | |
|---|---|---|
| | lowest | highest |
| NaNO₂ (sodium nitrite) | 10 | 10,000 |
| NADH | 50 | 10,000 |
| NADPH | 50 | 10,000 |
| Glutathione (oxidized form) | 50 | 10,000 |
| Hydrogen peroxide | 0.01% | 0.3% |
| Sodium Glucuronate | 10 | 10,000 |
| Isocitric | 10 | 10,000 |
| 2-Hydroxybutyric Acid | 10 | 10,000 |
| Glucose | 10 | 10,000 |
| Fructose | 10 | 10,000 |
| Lactose | 10 | 10,000 |
| Galactose | 10 | 10,000 |
| Cytochrome C | 10 | 10 |
| Phenazine Methosulfate | 10 | 10,000 |
| Dichlorophenolindophenol | 10 | 100 |
| FAD | 10 | 500 |
| FMN | 10 | 1000 |
| Triphenyltetrazolium Chloride | 10 | 1000 |

EXAMPLE 4

This example illustrates the minimal time of interaction between sphere suspension and stabilizing agent needed for stabilization of spheres.

Sodium bisulfite was selected as a typical stabilizing agent for use in this experiment. Protein spheres were formed as described in Example 2. Two concentrations of stock sodium bisulfite (0.05 and 0.1M) were used (5 μL added per mL of sphere suspension). Thereafter at the indicated times, 1.5 mL of N.S. was added to evaluate the effect of various incubation times on sphere stability. The results are provided in Table IV.

TABLE IV

Interaction Times to Stabilize Protein Spheres

| AGENT | INTERACTION TIME (hr) | FINAL CONCENTRATION OF AGENT | |
|---|---|---|---|
| | | 500 μM | 1000 μM |
| | | Time for solution to clarify | |
| Sodium Bisulfite | 0.17 | <1 min | 1 min |
| | 0.33 | 1 min | 3 min |
| | 0.50 | 5 min | 1 hr |
| | 1.00 | 2 hr | Turbid overnight |
| | 2 to 6 | Turbid overnight | Turbid overnight |

As can be seen from the results in Table IV, stability was not obtained with interaction time less than approximately 10 minutes. Additionally, a higher concentration of stabilizing agent is more effective in stabilizing spheres within a shorter time of interaction. In general, incubation of at least two hours will be needed. This shows that the stabilization process is a gradual one, suggesting a physical rearrangement of molecules within or on the surface of the spheres to render the spheres gradually more resistant to resolubilization.

EXAMPLE 5

This example illustrates that premixing a stabilizing agent with HSA solution before the addition of alcohol results in stable spheres.

To each of a series of tubes containing 1.0 mL of HSA solution (15% in normal saline), was added 30 μL of one of the following agents: sodium bisulfite (0.025 to 0.25M), DTT (0.025 to 0.1M), NADP (0.05 to 0.1M), thioctic acid (oxidized, 0.01 to 0.025M) and control solution (normal saline).

Ethanol (70%) was then added dropwise (approximately 1.7 to 1.88 mL) to form turbid suspensions. After 2 hours at room temperature, 5 mL of normal saline was added to see if the turbid suspensions became clear solutions. Only the control tube which had no stabilizing agent added before formation of the spheres reverted to a clear solution within 5 minutes. All other tubes were turbid after more than 2 hours.

Ethanol (70% in water) was added dropwise to a parallel set of tubes containing 1.0 mL of HSA solution (15% in normal saline) to form a turbid suspension, followed by the addition of 30 μL of the above mentioned agents at the above mentioned concentrations. After 2 hours at room temperature, 5 mL of normal saline was added to each tube. Again, only the control tube which had no stabilizing agent added after formation of the spheres reverted to a clear solution within 5 minutes. All other tubes were turbid after more than 2 hours. This result indicates that there is no significant difference between adding the stabilizing agent before or after the formation of the spheres.

To a third parallel set of tubes, 30 μL of the above mentioned agents were added to 1.0 mL of HSA (15%) without addition of alcohol. No turbidity was seen during or after the two hours observed. This result indicates that the agents only stabilized the spheres and did not by themselves cause the formation of spheres.

EXAMPLE 6

This example illustrates that protein particles can be stabilized by a hydrogen-accepting agent in the presence of a hydrogen-donating agent.

We have shown in the above experiments that a hydrogen-accepting (oxidized state) agent such as NADP can stabilize protein particles against resolubilization but that a similar molecule in the reduced state (NADPH) cannot.

Ethanol (70% in water) was added to HSA solution (15%) to produce turbidity. To aliquots of 1.0 mL of protein particle suspension was added 5 μL of the agent(s) (in molar concentrations) listed in Table V. After 2 hours, 5 mL of N.S. was added to each tube and the suspension was examined for turbidity.

TABLE V

Stabilization of Protein Particles Using Combinations of Hydrogen-Accepting and Hydrogen-Donating Agents

| Tube | NADP | NADPH | After addition of N.S. |
|---|---|---|---|
| 21 | 0 | 0 | clear |
| 22 | 0 | 0.1 | clear |
| 23 | 0.1 | 0 | turbid |
| 24 | 0.1 | 0.10 | turbid |
| 25 | 0.1 | 0.25 | turbid |
| 26 | 0.1 | 0.50 | turbid |

As Table V indicates, a hydrogen-accepting agent (NADP) is effective in stabilizing protein spheres in the presence of a hydrogen-donating agent (NADPH).

EXAMPLE 7

This example illustrates that the addition of chemotherapeutic agents does not interfere with sphere formation or stabilization.

Adriamycin was added to HSA (15%) to result in a concentration of 0.1 mg/mL. Control HSA was 15% without adriamycin.

Ethanol (70%) was added to the HSA solutions until the solutions became turbid. Thereafter, 10 µL of sodium bisulfite (0.05M to 0.5M) was added per 1.0 mL of suspension. After 2 hours incubation, 5 mL of N.S. was added and the mixtures were examined for resolubilization of the protein spheres.

The results showed that both control spheres and spheres with adriamycin were stable against resolubilization. Incorporation of adriamycin in the spheres did not interfere with the action of the stabilizing agent.

EXAMPLE 8

This example illustrates that enzymes incorporated within the interior or on the surface of the protein particles, are still active after the particles have been stabilized by the addition of a stabilizing agent.

To demonstrate that enzymes trapped within the interior and on the surface of protein particles stabilized with a stabilizing agent can retain their catalytic function, 5 µL of a commercial preparation of peroxidase was added to 1 mL of a HSA solution (15%). Ethanol (70%) was subsequently added to produce protein spheres. Within 5 minutes, 5 µL of sodium bisulfite (0.1M) was added to 1.0 mL of the suspension to stabilize the spheres. After overnight incubation, the spheres were washed three times in normal saline (10 mL each time) without resolubilization.

A solution containing a peroxidase substrate was added to the sphere suspension. A strongly positive reaction (read at 490 nm wavelength) was produced within 5 min. As a control, a portion of the supernatant from the final wash was incubated with the peroxidase substrate. The reaction was negative, indicating that the peroxidase reactivity observed resided with the spheres and not from any residual enzyme in the supernatant.

This experiment did not prove whether all the enzymes were inside the spheres or whether some were exposed on the surface of the particles. However, the addition of a stabilizing agent did not result in substantial loss of enzyme activity.

EXAMPLE 9

This example illustrates that antigenic sites of proteins within the interior and surface of spheres remain unchanged for reaction with the specific antibody even after stabilization of the spheres with a stabilizing agent.

Rabbit IgG was chosen as the antigen A goat anti-rabbit (GAR)IgG (conjugated to peroxidase) was used as the antibody. The protocol in Example 9 was followed except that rabbit IgG was incorporated within the spheres and on their surfaces instead of the peroxidase enzyme.

The rabbit IgG-containing spheres were washed three times in normal saline (10 mL each time), and a diluted aliquot of GAR was added to the sphere suspension. After incubation at 37° C. for 1 hr, unreacted GAR was removed by three additional washes in normal saline (10 mL each). The supernatant of the last wash was checked for any residual GAR activity, which may represent excess GAR, or leakage of GAR complexed with rabbit IgG that resulted from partial resolubilization of the particulates.

The result showed that the spheres, but not the supernatant, had peroxidase activity. This experiment suggested that the spheres may be porous enough for some GAR to penetrate the surface of the spheres to bind to the rabbit IgG inside the spheres. Alternatively, enough rabbit IgG antigenic sites may be exposed on the surface of the spheres to allow enough GAR binding for easy detection.

EXAMPLE 10

This example illustrates that antibodies are still reactive within the interior and surface of the albumin spheres even after stabilization of the spheres by a stabilizing agent.

The protocol of Example 9 was used except that an antibody was incorporated instead of an antigen. As an example of antibody, a commercial source of polyclonal goat anti-human fibrinogen IgG was used. The suspension of antibody-containing spheres (1.0 mL) was incubated overnight with sodium bisulfite (5 µL of a 0.05M solution). The resulting particulates were washed three times with normal saline (10 mL each) without resolubilization. Control spheres were similarly prepared except without any incorporated antibody.

The sphere pellets were then resuspended in a human fibrinogen solution (0.01 mg/mL) for 2 hr at room temperature, after which the spheres were washed again twice to remove excess fibrinogen (the antigen).

For detection of antigen binding, a mouse anti-human fibrinogen (MAH) monoclonal antibody was used to react with the spheres for 2 hours, followed by removal of the MAH by washing twice. Subsequently, a sheep anti-mouse IgG (conjugated to peroxidase) was used to detect the presence of mouse monoclonal antibody-human fibrinogen complex on or within the spheres.

The result showed that the supernatant of the last wash was negative, but the spheres showed positive reactivity indicating that the primary antibody (goat anti-human fibrinogen IgG) was present within or on the surface of the spheres even after multiple washings.

EXAMPLE 11

This example illustrates that enzymes, antigen and antibodies can be added during the stabilization phase to spheres without loss of activity.

The protocol of Examples 8, 9 and 10 for enzyme, antigen and antibody were repeated, respectively, except that spheres were first formed without the respective biological agent. The respective biological agents were added within 30 seconds of the addition of the stabilizing agent. All the subsequent washings and reagents used were identical.

The results again showed that enzymes, antigens and antibodies could be stabilized essentially on the surfaces of the spheres during the stabilization process and maintain their biological functions.

EXAMPLE 12

This example shows that DNA/RNA can be incorporated inside and on the surface of protein spheres before stabilization with a stabilizing agent.

A commercial preparation of calf thymus DNA was added to HSA (15%) to provide a concentration of 5 µg of DNA per mL. Control spheres were formed with HSA without DNA. Ethanol (70%) was added to produce turbidity. The spheres thus formed were stabilized by incubating the mixtures overnight with 5 µL of sodium bisulfite (0.1M) per mL suspension.

The spheres were then washed in normal saline (3×10 mL) and digested in trypsin to release any DNA previously incorporated inside or on the surface of spheres. Detection of DNA was performed by the Intvogen DNA DipStick Kit, which showed strong positivity with the trypsin digest of spheres prepared from DNA-containing HSA solutions, but not from control spheres or the supernatants of both experimental and control sphere suspensions.

The experiment was repeated with RNA where all the reagents were also added a RNAase inhibitor. The findings were similar to DNA spheres.

These experiments showed that the spheres can be used as stable carriers for gene therapy for either in vitro or in vivo experiments and therapy.

EXAMPLE 13

This examples illustrates that DNA and RNA can bind to spheres during the stabilizing phase.

The experimental protocol of Example 12 was followed except that protein particles were first formed by addition of ethanol (70%) to 1.0 mL of HSA (15%) in the absence of DNA or RNA (with RNAase inhibitor). Within 0.5 rain of addition of the stabilizing agent (sodium bisulfite 0.1M), 5 μL of a suspension of DNA or RNA was added to the protein spheres to result in a final concentration of 5 μg DNA/RNA per mL of protein suspension.

After digestion of the spheres with trypsin, the protein solution was checked for the presence of liberated DNA or RNA. Only spheres which had DNA or RNA added at the stabilization phase showed strong positivity. Control spheres or the supernatant of the last wash from either the experimental spheres or control spheres gave negative results when tested for the presence of DNA or RNA.

EXAMPLE 14

Additional agents representative of different chemical groups were used to determine their ability to stabilize spheres formed by adding 70% ethanol to a 15% HSA solution. 20 microliters of a 1M or 1 mM solution of the potential stabilizing agent was added to 2 mL of sphere suspensions. Only two final concentrations (10 mM and 10 micromolar) of the agents in the sphere suspensions were studied initially for screening purposes. After two hours of incubation, 5 mL of normal saline was added to 2 mL of sphere suspension. A change from turbidity back to a clear solution indicated that the spheres were not stabilized by either concentration of the agents used. If turbidity remained after 30 minutes, a wider concentration of effective agents was added to sphere suspensions to determine the minimal final concentration that could stabilize the spheres. The agents were as follows:

Anions:
   ammonium chloride
   ammonium nitrate
   ammonium sulfate
   ammonium phosphate, monobasic and dibasic
   potassium iodide
   potassium acetate
   potassium bicarbonate
   molybdic acid, sodium salt
Cations:
   cobalt chloride
   cupric chloride
   magnesium chloride
   manganese chloride
   ferric nitrate
Vitamins:
   cyanobalamin ($B_{12}$)
   ergocalcifero ($D_2$)
Acids:
   folinic acid
   δ-aminolevulinic acid
   boric acid
   cholic acid
Amino acids:
   D,L-phenylalanine
   poly-L-lysine, MW 114,700 and MW 430,500
Carbohydrates:
   2-amino-2-deoxy-D-galactopyranose
Antibiotics:
   penicillin, sodium salt
   gentamycin
   chloramphenicol
N-acetyl compounds:
   N-acetylneuraminic acid
   w-acetamido-2-deoxy-D-glucose
Amines:
   ethanolamine
Others:
   choline bitartrae
   cephalothin
   glycerol
   heparin
   chear germ agglutinin (lectin)
   D-sorbitol
   laminin
   dimethyl sulfoxide Results: All of the agents except the following were ineffective in stabilizing spheres either at the final concentration of 10 mM or 10 micromolar:

TABLE VI

| Effective Agents | Minimal Final Concentration (mM) |
| --- | --- |
| magnesium chloride | 5 mM |
| manganese chloride | 0.5 mM |
| γ-aminolevulinic acid | 0.002 mM |
| gentamycin | 0.05 mg/mL |
| poly-L-lysine, MW 147,000 | 0.1 mg/mL |
| poly-L-lysine, MW 430,500 | 0.1 mg/mL |
| N-acetylneuraminic acid | 0.5 mg/mL |
| dimethyl sulfoxide | 1/100 dilution |

Samples of suspensions were examined under the microscope and found to consist of monodispersed spheres with no aggregates seen.

EXAMPLE 15

Interaction of Na Bisulfite with 15% HSA Before Adding Alcohol to Form Spheres

I. Rationale

Previous examples show that Na bisulfite stabilizes the microspheres. In this study, the HSA solution was preincubated with Na bisulfite for different time spans before adding alcohol, and examines the effect on the stability of the resulting spheres.

II. Procedure

1. Incubate 1 mL of 15% HSA with 25 μL of 0.1 or 0.05M Na bisulfite for 5, 10, 20, 30, 60, and 120 minutes, respectively, before adding 70% ethanol to form spheres.

2. 1 and 60 minutes after forming spheres, add 3× volume (7.5 mL) of normal saline and shake well.

3. Record the time needed to dissolve the spheres.

III. Results

The times needed to redissolve the spheres was as follows.

TABLE VII

| Incubation | Adding normal saline 1 minute after forming spheres | | Adding normal saline 60 minutes after forming spheres | |
|---|---|---|---|---|
| Time (minutes) | 0.05M NaHSO$_3$ | 0.1M NaHSO$_3$ | 0.05M NaHSO$_3$ | 0.1M NaHSO$_3$ |
| 5 | immediately | immediately | 2 hours | more than 8 hours |
| 10 | immediately | immediately | 2.5 hours | more than 8 hours |
| 20 | immediately | immediately | 2.5 hours | more than 8 hours |
| 30 | immediately | immediately | 2.5 hours | more than 8 hours |
| 60 | immediately | immediately | 2.5 hours | more than 8 hours |
| 120 | immediately | immediately | 2 hours | more than 8 hours |
| Control (no NaHSO$_4$) | immediately | | immediately | |

IV. Discussion

1. The data show that pre-incubation of Na bisulfite in a solution of HSA for up to two hours did not improve the stability of the spheres if challenged within one minute of formation of spheres. In contrast, the incubation time of the spheres with Na bisulfite made a difference.

2. One minute of interaction of this agent with spheres is not sufficient for stabilization. However, if normal saline was added after 2 hours of incubation, the spheres were stable against resolubilization.

3. A final concentration of 2.4 millimolar Na bisulfite is more effective than a final concentration of 1.2 millimolar in promoting the stability of the spheres.

EXAMPLE 16

Pre-mixing Na Bisulfite with Ethanol Before Making Spheres

I. Purpose

To study the possibility of premixing Na bisulfite with ethanol before making the spheres and to study the stability of these spheres.

II. Procedure

1. Make 1, 0.5, 0.25, 0.1, 0.05, 0.025, 0.0125, 0.00625, 0.003125, 0.0015625, 0.00078125, and 0.000390625M Na bisulfite solutions in 70% ethanol.

2. Add the Na bisulfite containing alcohol solutions to 1 mL of 15% HSA to make spheres. Monitor the amount of alcohol solution needed.

3. Incubate for 2 hours.

4. Check the appearance of the sphere suspensions grossly and microscopically.

5. Add 3× volume of normal saline, mix well, and check the stability of the spheres.

III. Result

1. The Na bisulfite did not dissolve in 70% ethanol well. The highest concentration obtainable was 0.05M solution.

2. The amount of alcohol needed to make spheres remained the same as with pure 70% ethanol, regardless of the concentration of Na bisulfite. It took about 1.5 mL of alcohol/Na bisulfite solution per 1 mL of 15% HSA to make spheres.

3. Appearance after incubating for 2 hours was as follows:

TABLE VIII

| NaHSO$_4$ Concentration (μM) | | Appearance After 2 Hours | | After Adding Normal Saline |
|---|---|---|---|---|
| In Ethanol | In Suspension | Gross | Microscopic | |
| 50,000 | 30,000 | gelatinous | aggregates | precipitation |
| 25,000 | 15,000 | gelatinous | aggregates | precipitation |
| 12,500 | 7,500 | gelatinous | aggregates | precipitation |
| 6,250 | 3,750 | turbid 5+ | aggregates | turbid 4+ |
| 3,125 | 1,875 | turbid 5+ | aggregates | turbid 4+ |
| 1,562 | 937 | turbid 5+ | aggregates | turbid 4+ |
| 781 | 468 | turbid 5+ | aggregates | turbid 3+ |
| 390 | 234 | turbid 5+ | aggregates | turbid 2+ |
| 195 | 117 | turbid 4+ | no aggregate | turbid 2+ |
| 98 | 58 | turbid 4+ | no aggregate | turbid 1+ |
| 48 | 29 | turbid 3+ | no aggregate | turbid 1+ |
| 24 | 14 | turbid 2+ | no aggregate | dissolved |
| 0 | 0 | turbid 3+ | individual spheres | dissolved |

IV. Discussion

These results show that the spheres can be stabilized by premixing the ethanol with the reducing agent, i.e., Na bisulfite. The optimal concentrations are between approximately 29 and 117 micromolars in the suspension.

EXAMPLE 17

Ability of Spheres Stabilized by Na Bisulfite to Bind Fibrinogen

This example shows that protein molecules other than albumin (e.g., fibrinogen) can be bound on the surface of the spheres in the presence of a stabilizing agent and that there is an optimal time for the addition of these surface molecules after the formation of the spheres.

Occasionally it is necessary to bind large quantities of certain biological molecules (such as fibrinogen) on the surface of spheres (to serve as platelet substitutes), but such biological molecules may have limited solubility in its preparative medium. Therefore, a large volume of the biological solution (at the highest possible concentration) will have to be mixed with the spheres soon after their formation. Mixing in a large volume of such non-alcohol containing solution to a particularly stabilized sphere suspension may redissolve some of the spheres. However, if the biologically active molecule solution is added after the spheres were completely stabilized by the stabilizing agent may result in unstable or insufficient binding of the biologically active molecule on a per sphere basis. This experiment demonstrates the effectiveness of binding fibrinogen using three different methods of stabilizing the spheres.

I. Procedure

1. Make spheres by adding Na bisulfite in one of the following methods:

a. to 15% HSA before adding 70% ethanol;

b. to 70% ethanol before adding 15% HSA; or c. within 1 minute after forming the spheres by adding 70% ethanol to 15% HSA.

2. The final Na bisulfite concentration in all three methods will be about 1 mM.

3. Add 0.5× volume of 0.5 mg/mL fibrinogen 10, 30, 60, and 120 minutes after the spheres are formed per 1.0 volume of sphere suspension.

4. Compare the amount of fibrinogen bound per billion spheres, by using a special ELISA method for measuring fibrinogen content.

II. Results

TABLE IX

| Time of Adding Fibrinogen (minutes) | Concentration of Spheres (× $10^{-9}$/mL of Suspension) Prepared by Adding NaHSO$_4$ | | |
|---|---|---|---|
| | in HSA | in Ethanol | After Forming Spheres |
| 10 | (All spheres dissolved after adding fibrinogen.) | | |
| 30 | (Part of the spheres dissolved after adding fibrinogen. All spheres then dissolved during the washing process.) | | |
| 60 | 4.399 | 4.164 | 2.485 |
| | 4.277 | 4.175 | 2.388 |
| 120 | 3.945 | 5.842 | 3.474 |
| | 3.876 | 5.802 | 3.474 |

TABLE X

| Time of Adding Fibrinogen (minutes) | Mean Diameter (μm) of Spheres Prepared by Adding NaHSO$_4$ | | |
|---|---|---|---|
| | in HSA | in Ethanol | After Forming Spheres |
| 60 | 1.018 | 1.078 | 1.191 |
| | 1.018 | 1.081 | 1.195 |
| 120 | 1.278 | 1.260 | 1.193 |
| | 1.282 | 1.261 | 1.193 |

TABLE XI

| Time of Adding Fibrinogen (minutes) | Fibrinogen Bound (mg/l × $10^{-9}$ Spheres) in Spheres Prepared by Adding NaHSO$_4$ | | |
|---|---|---|---|
| | in HSA | in Ethanol | After Forming Spheres |
| 60 | 0.078 | 0.080 | 0.106 |
| 120 | 0.085 | 0.023 | 0.116 |

IV. Discussion

1. The spheres had to be incubated in the stabilizing agent for more than 30 minutes to stabilize the spheres.
2. All three different methods of adding stabilizing agent could bind fibrinogen onto the spheres.
3. When the stabilizing agent was premixed in HSA before adding alcohol to form spheres, the timing of adding fibrinogen had no effect on the amount of fibrinogen bound.
4. When the stabilizing agent was pre-mixed in the alcohol before mixing with HSA solution to form spheres, the ability of the spheres to bind fibrinogen diminished with time.
5. When the stabilizing agent was added after the spheres were formed, the timing of adding fibrinogen had no effect on the amount of fibrinogen binded per sphere.
6. In terms of fibrinogen/sphere, adding the stabilizing agent after the spheres were formed resulted in more fibrinogen bound per billion spheres than the other two methods.

For albumin-based particles, additional substances serving a therapeutic or diagnostic function, or both, can be entrapped within the particle bulk and carried by the particles to a site for in vivo administration. Examples of classes of such substances are enzymes, amino acids, peptides, nucleic acids, contrast agents and nonmacromolecular therapeutic drugs. A contrast agent of particular interest is technetium. The incorporation of these additional substances is conveniently achieved by combining them with the protein solutions from which the proteins are precipitated to form the particles.

Additional substances can also be attached non-covalently to the exterior surfaces of the particles. Examples of substances which are useful when adhered to the particles in this manner are proteins, immunoglobulins and nucleic acids, as well as molecular species in general which exhibit specific binding to biological molecules such as cell surface receptors. Specific examples of particular interest are fibrinogen and peptides which contain reactive sequences of fibrinogen, such as aspartine-glycine-aspartic acid (RGD). Adherence of these substances to the particle surfaces is conveniently achieved by contacting the substances with the particles soon after the particles are formed.

The following is a list of examples of specific substances which can be incorporated into the composition of particles of the present invention.

1. Protein A
2. Concanavalin A
3. IgG
4. hemagglutinin
5. transfer fin
6. von-Willebrand factor
7. anti-human factor IX monoclonal antibody
8. anti-CD8 monoclonal antibody
9. goat anti-clathrin
10. fibronectin
11. human fibroblast growth factor-acidic, recombinant
12. human interleukin-2, recombinant
13. anti-human platelet-derived growth factor beta receptor
14. anti-beta-lipoprotein
15. alpha 2-macroglobulin
16. streptokinase
17. anti-progesterone antibody
18. anti-leukotriene B4 antibody
19. CGGRGDF-NH$_2$
20. doxorubicin
21. daunarubicin
22. EDTA-conjugated to HSA
23. DTPA-conjugated to HSA
24. technetium
25. gadolinium
26. HSA conjugated to FITC (Fluorescein Isothiocyanate)
27. HSA conjugated to TRITC (Tetramethylrhodamine B isothiocyanate)
28. HSA conjugated to PE (Phycoerythrin)
29. HSA conjugated to Ferritin
30. HSA conjugated to biotin
31. alkaline phosphatase
32. peroxidase
33. amphotericin B
34. Adjuvant peptide (N-acetylmuramyl-1-alanyl-d-isoglutamine)
35. HIV-1 protease substrate (acetyl-ser-gln-asn-tyr-pro-val-val-amide)
36. Fe$_3$O$_4$ magnetite or magnetic particles
37. cysteine-cyclohexanol conjugate 38. HIV-glycoprotein 120
39. anti-CD4 antibody
40. fibrinogen Albumin-based particles containing Tc99m either in their bulk or on their surfaces are illustrative of the use of these particles as vehicles for specific agents. The incorporation or attachment of Tc99m can be achieved through direct covalent bonding or through a chelating agent. Examples of chelating agents are cysteine-cyclohexanol conjugate and DTPA.

The chelating agent may be pre-bonded to soluble HSA molecules which are then mixed with other HSA molecules during the formation of the original aqueous protein solution. Alternatively, chelating agents may be covalently bonded directly to preformed particles. A third alternative is to add the chelating agent as one of the biological molecules, not covalently bound to any HSA molecules. The chelating agent will then be trapped within the particles or near their surfaces when the particles are formed.

The procedure of binding the Tc99m to the particles, with or without chelating agents, can follow standard nuclear medicine procedures. For example, stannous chloride or other reducing agents (0.01 to 0.3 mg) can be added to approximately 1 mg of particles suspended in a suitable buffer to reduce the sulhydryl groups in the protein molecules. Sodium pertechnetate Tc99m (5 to 250 millicurie) is then added to the suspension. The excess reducing agent reduces the pertechnetate ($TcO_4^-$) to $TcO_2^-$, which then binds to the sulhydryl group on the protein molecules, or to the sites on the chelating agents designed to bind the $TcO_2^-$. It is expected that more Tc99m binds to particles through chelating agents than without chelating agents.

Alternatively, stannous chloride and lyophilized particles could be stored as a dry powder in the absence of oxidizing agents, to be reconstituted as a suspension by the addition of Tc99m solutions.

The presence of chelating agents has the additional advantage of possibly stabilizing the $TcO_2^-$ before it binds to the protein molecules.

An alternative method would be to allow pertechnetate Tc99m to be reduced by a reducing agent in the presence of a free chelating agent, i.e., one which is not yet associated with the particles, then binding the Tc99m-chelating agent conjugate to the particles.

The particles may alternatively be reduced by a different reducing agent after which they can be purified and stored as a reduced dry (lyophilized) powder, while the pertechnetate would be reduced by a different kind of reducing agent immediately before interaction with the already reduced particles. Due to the short half life of Tc99m, the product which results from the mixing of the pertechnetate-containing liquid with the particle suspension or powder should be ready for injection into a patient within much less than one hour and without the need for other purification. Examples of reducing agents are dithiothreitol, dithioerythritol, ascorbic acid, 2-mercaptoethanol, and pyrophosphate. In addition, the reduced $TcO_2^-$ may first be stabilized by an intermediate product involving D-glucarate.

A wide variety of bioactive molecules can be incorporated within the interior, on the surface, or near the surface of the particles. Combinations of one or more compounds can also be incorporated into a single particle.

Examples of biologically active molecules that can be incorporated include, but are not limited to: drugs, biologically active peptides, polypeptides, carbohydrates, lipids, lipoproteins, glycoproteins, enzymes, ligands, receptors, radioactive compounds, fluorescent or excitable compounds, imaging materials, oxygen-carrying materials, toxins, antitoxins, neurologically active materials, chemotherapeutic agents, chelating compounds, nucleotides, nucleoside, nucleic acids, polynucleotides, antibiotics, magnetic materials, and nutrients. Further examples are subunits or fragments of these molecules, as well as analogs of the molecules, their competitors, inhibitors, and antagonists, antibodies against them, antibodies against antibodies against them, receptors to which they will bind, anti-sense entities (whether in the form of RNA, DNA or even protein forms), and the genes from whose information they are derived.

The following are examples of biologically active molecules which can be incorporated in the manner described above.

Lipids:
methanoic, ethanoic, propanoic, butanoic, pentanoic, hexanoic, heptanoic, octanoic, nonanoic, decanoic, undecanoic, dodecanoic, tridecanoic, tetradecanoic, pentadecanoic, hexadec. anoic, heptadecanoic, octadecanoic, nonadecanoic, eicosanoic, heneicosanoic, docosanoic, tricosanoic, tetracosanoic, pentacosanoic, heXacosanoic, heptacosanoic, octacosanoic, nonacosanoic, triacontanoic, hentriacontanoic, 10-undecenoic, cis-9-tetradecenoic, trans-9-tetradecenoic, cis-10-pentadecenoic, cis-9-hexadecenoic, trans-9-hexadecenoic, cis-10-heptadecenoic, cis-6-octadecenoic, trans-6-octadecenoic, cis-7-octadecenoic, cis-9-octadecenoic, trans-9-octadecenoic, cis-11-octadecenoic, trans-11-octadenenoic, cis-12-octadecenoic, cis-13-octadecenoic, cis-12-hydroxy-9-octadecenoic, trans-12-hydroxy-9-octadecenoic, cis-9,12-octadecadienoic, trans9,12-octadecadienoic, 9,11(10,12)-octadecadienoic, cis-6,9,12-octadecatrienoic, cis-9,12,15-octadecatrienoic, cis-6,9,12,15-octadecatetraenoic, cis-10-nonadecenoic, cis-5-eicosenoic, cis-8-eicosenoic, cis-11-eicosenoic, cis-13-eicosenoic, cis-11,14-eicosadienoic, cis-5,8,11-eicosatrienoic, 5,8,11-eicosatriynoic, cis-8,11,14-eicosatrienoic, cis-11,14,17-eicosatrienoic, cis-5,8,11,14-eicosatetraenoic, 5,8,11,14-eicosatetraynoic, cis-5,8,11,14,17-eicosapentaenoic, cis-13-docosenoic, trans-13-docosenoic, cis-13,16-docosadienoic, cis-13,16,19-docosatrienoic, cis-7,10,13,16-docosatetraenoic, cis-4,7,10,13,16,19-docosahexaenoic, cis-15-tetracosenoic acids.

Lectins:
Abrus precatorius (Agglutinin, Abrin A toxin, Abrin C toxin), Agaricus bisporus, Anguilla anguilla, Arachis hypogaea, Bandeiraea simplicifolla (BS-I, BS-I-B4, BS-I-AB3, BS-I-A2B2, BS-I-A3B, BS-I-A4, BS-II), Bauhinia purpurea, Caragana arborescens, Cicer arietinum, Codium fragile, Concanavalin A, Succinyl-Concanavalin A, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus (Bacterial agglutinin), Lycopersicon esculentum, Maclura pomifera, Momordica charantia, Mycoplasma gaillsepticum, Naja mocambique mocambique, Naja naja kaouthia, Perseau americana, Phaseolus coccineus, Phaseolus limensis, Phaseolus vulgaris (PHA-E, PHA-L), Phytolacca americana, Pisum sativum, Pseudmonas aeruginosa PA-I, Psophocarpus tetragonolobus, Ptilota plumosa, Ricinus communis (Toxin, RCA60, Toxin, RCA120), Robinia pseudoacacia, Sambucus nigra, Solanum tuberosum, Sophora japonica, Tetragonolobus purpureas, Triticum vulgaris, Ulex europaeus (UEAI, UEAII), Vicia faba, Vicia sativa, Vicia villosa (A4, B4), Vigna radiata, Viscum album, Wisteria floribunda.

Complement proteins, either as single proteins or as combinations of several proteins:

C1q, C2, C3, C4, C5, C6, C7, C8, C9, Properdin factor B.

Spin labels and spin traps:

Doxyl Nitroxides, e.g., 3-beta-doxyl-5-alpha-cholestane;

Proxyl Nitroxides, e.g., 3-(4-nitrophenoxycarbonyl)-proxyl;

Tempo Nitroxides, e.g., Tempo;

DL-t-Butyl Nitroxide;

Spin traps: Nitrosobenzene, Nitrosadisulfonic acid, 2-methyl-2-Nitroso-Propane.

Arachidonic acid cascade and related compounds:

HETEs: 5(S)-HETE[5(S)-hydroxy-6-trans-8-cis-11-cis-14-cis-eicosatetraenoic acid]; 11(S)-HETE[11(S)-hydroxy-5-cis-8-cis-12-trans-14-cis-eicosatetraenoic acid]; 12(R)-HETE[12(R)-hydroxy-5-cis-8-cis-10-trans-14-cis-eicosatetraenoic acid]; 12(S)-HETE[12(S)-hydroxy-5-cis-8-cis-10-trans-14-cis-eicosatetraenoic acid]; 15(S)-HETE[15(S)-hydroxy-5-cis-8-cis-11-cis-13-trans-eicosatetraenoic acid];

HPETEs: 5(S)-HPETE [5(S)-hydroperoxy-6-trans-8-cis-11-cis-14-cis-eicosatetraenoic acid]; 12(S)-HPETE[12(S)-hydroperoxy-5-cis-8-cis-10-trans-14-cis-eicosatetraenoic acid]; 15(S)-HPETE [15(S)-hydroperoxy-5-cis-8-cis-11-cis-13-trans-eicosatetraenoic acid];

DiHETEs: 5(S),6(R)-DiHETE[5(S),6(R)-dihydroxy-7-trans-9-trans-11-cis-14-cis-eicosatetraenoic acid]; 5(S), 12(S)-DiHETE[5(S), 12(S)-dihydroxy-6-trans-8-cis-10trans-14-cis-eicosatetraenoic acid]; 5(S), 15(S)-DiHETE[5(S), 15(S)-dihydroxy-6-trans-8-cis-11-cis-13-trans-eicosatetraenoic acid];

Other arachidonic acid cascade related compounds:

13-Azaprostanoic acid; Baicalein; 7-7-dimethyleicosadienoic acid; 5,8,11-eicosatriynoic acid; 5,8,11,14-eicosatetraynoic acid; oleoyloxyethyl Phosphocholine; sodium furegrelate; w-3 fatty acids; leukotrienes (LTA4, LTB4, LTC4, LTD4, LTE4); lipoxin (A4, B4), Prostaglandins (A2, B2, D2, E1, E2, F2α, I2, G2, H2); 16-16-Dimethyl-prostaglandin E2; 6-Ketoprostaglandin F1α; 2,3-Dinor 6-keto-prostaglandin F1α; 9,11-Dideoxy-9α,11α-methanoepoxyprostaglandin-F2α; Carbacyclin; Thromboxanes (CTA2, B2, A2); p-Arbutin; H-Arg-gly-Asp-OH; H-Arg-Gly-Asp-Ser-Pro-Ala-Ser-Ser-Lys-Pro-OH; Ascorbate oxidase; ascorbic acid; asparagine; aspartic acid; arachidonic acid Ion channel modulators:

Amiloride, Baicalein, BAY K 8644, Bepridil, Brevetoxin (PbTx-1, PbTx-2, PbTx3, PbTx-7, PbTx-9), w-Conotoxin GVIA, Conus geographus, Diltiazem, Methoxyverapamil, Nifedipine, Ryanodine, 9,21,-Dehydro-Ryanodine, Saxitoxin, Tetrodotoxin, TMB-8, Toxin II, Verapamil.

Biologically active peptides:

4-(2-Acetamido-2-deoxy-beta-D-Glucopyranosyl)-N-acetylmuramyl-L-Ala-D-Glu Amide

N-Acetyl-Asp-Glu

N-Acetyl-Cholecystokinin and its fragments

N-Acetyl-Hirudin and its fragments

Acetyl-Leu-Leu-Argininal

N-Acetyl-Leu-Leu-Methioninal

N-Acetyl-Leu-Leu-Norleucinal

Acetyl-Met-Asp-Arg-Val-Leu-Ser-Arg-Tyr

N-Acetyl-Met-Leu-Phe

N-Acetylmuramyl-D-alanyl-D-isoglutamine

N-Acetylmuramyl-L-alanyl-D-isoglutamine

N-Acetylmuramyl-L-alanyl-L-isoglutamine

N-Acetylmuramyl-Ala-D-isoglutaminyl-Ne-stearoyl-Lys

N-Acetyl-Phe-Nle-Arg-Phe Amide

Acetyl-Renin Substrate Tetradecapeptide

Acetyl-Ser-Asp-Lys-Pro

Acetyl-Ser-Gln-Asn-Tyr

Acetyl-Ser-Gln-Asn-Tyr-Pro-Val-Val Amide

Acetyl-Ser-Tyr-Ser-Met-Glu-His-Phe-Arg-Trp-Gly-Lys-Pro-Val Amide

N-Acetyl-Thr-Ile-Nle-Phe(CH$_2$NH)-Nle-Gln-Arg Amide

ACTH (Adrenocorticotropic Hormone)

Adrenal Cyclase Activating Polypeptide-27

Adrenal Medulla Peptides

Adrenal Peptide E

Adrenocorticotropic Hormone and fragments

Adrenorphin

Adipokinetic Hormone II

Adjuvant Peptide

Ala-Arg-Pro-Gly-Tyr-Leu-Ala-Phe-Pro-Arg-Met Amide beta-Ala-Arg-Ser-Ala-Pro-Thr-Pro-Met-Ser-Pro-Tyr Ala-D -gamma-Glu-Lys-D-Ala-D-Ala Ala-Gly-Cys-Lys-Asn-Phe-Phe-Trp-Lys-Thr-Phe-Thr-Ser-Cys Ala-Gly-Ser-Glu Ala-D-isoglutaminyl-Lys-D-Ala-D-Ala Ala-Leu-Ala-Leu Ala-Leu-Ile-Leu-Thr-Leu-Val-Ser Ala-Lys-Pro-Ser-Tyr-Hyp-Hyp-Thr-Tyr-Lys Ala-Ser-His-Leu-Gly-Leu-Ala-Arg beta-Ala-Ser-His-Leu-Gly-Leu-Ala-Arg Ala-Ser-Thr-Thr-Thr-Asn-Tyr-Thr D-Ala-Ser-Thr-Thr-Thr-Asn-Tyr-Thr Amide Aldosterone Secretion Inhibiting Factor Allatotropin Alytesin Amastatin beta-Amyloid and fragments Angiogenin and fragments Angiotensin I and analogs Angiotensin II and analogs Angiotensin III and analogs Angiotensin Converting Enzyme Inhibitor Angiotensinogen and fragments Angiotonin Anorexogenic Peptide Anthranilyl-His-Lys-Ala-Arg-Val-Leu-p-Nitro-Phe-Glu-Ala-Nle-Ser Amide Antide Anti-inflammatory Peptide 1

Antipain

Antireproductive Tripeptide
Apamin
Arg-Arg-Leu-Ile-Glu-Asp-Ala-Glu-Tyr-Ala-Ala-Arg-Gly
Arg-Arg-Leu-Ile-Glu-Asp-Asn-Glu-Tyr-Thr-Ala-Arg-Gly
Arg-Arg-Lys-Ala-Ser-Gly-Pro
Arg-Gly-Asp
Arg-Gly-Asp-Ser
Arg-Gly-Asp-Ser-Pro-Ala-Ser-Ser-Lys-Pro
Arg-Gly-Glu-Ser
Arg-Gly-Phe-Phe-Tyr-Thr-Pro-Lys-Ala
Arg-Gly-Pro -Phe-Pro-Ile
Arg-His-Phe
Arg-Lys-Arg-Ala-Arg-Lys-Glu
Arg-Lys-Asp-Val-Tyr
Arg-Lys-Glu-Val-Tyr
Arg-Phe-Asp-Ser
Arg-Pro-Lys-Pro-Gln-Gln-Phe-Phe-Gly-Leu-Met Amide
Arg-Pro-Pro-Gly-Phe-Ser-Pro-Phe-Arg
Arg-Ser-Arg-His-Phe
Arg-Tyr-Leu-Pro-Thr
Arg-Tyr-Val-Val-Leu-Pro-Arg-Pro-Val-Cys-Phe-Glu-Lys-Gly-Met-Asn-Tyr-Thr-Val-Arg
Asn-Ala-Gly-Ala
Asn-Pro -Asn-Ala-Asn-Pro-Asn-Ala
Asn-Pro-Asn-Ala-Asn-Pro-Asn-Ala-Asn-Pro-Asn-Ala
Asp-Ala-Glu-Asn-Leu-Ile-Asp-Ser-Phe-Gln-Glu-Ile-Val
Asp-Arg-Val-Tyr-Ile-His-Pro-Phe-His-Leu
Asp-Leu-Trp-Gln-Lys
Asp-Ser-Asp-Pro-Arg
Atrial Natriuretic Peptide and fragments
Atriopeptins
Auriculin
Avidin
Beauvericin
Bestatin
Biocytin-Neuropeptide Y
Biotin/biotinylated peptides
N-t-BOC-beta-Ala-Trp-Met-Asp-Phe Amide
N-t-BOC-beta-Ala-Trp-Met-beta-(Benzyl)Asp-Phe Amide
N-t-BOC-Gly-Trp-Met-Asp-Phe Amide
N-t-BOCGly-Trp-Met-beta-(benzyl)Asp-Phe Amide
N-t-BOC-Glu-Glu-Ile Methyl Ester
N-t-BOC-Glu-Glu-Leu Methyl Ester
N-t-BOC-Glu-Glu-Val Methyl Ester
N-t-BOC-Lys-Pro-Tyr-Ile-Leu Methyl Ester
N-t-BOC-Met-Asp-Phe Amide
N-t-BOC-Met-Leu-Phe
N-t-BOC-Nle-Leu-Phe
N-t-BOC-Phe-D-Leu-Phe
N-t-BOC-Phe-Leu-Phe-Leu-Phe
N-t-BOC-Trp-Asp-Phe Amide
N-t-BOC-Trp-Met-Asp-Phe Amide
N-t-BOC-Trp-Met-Phe Amide
Bombesin and analogs
Bradykinin and analogs
Bradykinin Potentiator (e.g. 5a, 9a, B, C)
Brain Natriuretic Peptide
Brefeldin A
Buccalin
Bursin
Caerulein
Calcitronin
Calcitonin Gene Related Peptide
beta-Calcitonin Gene Related Peptide
Calcitonin Gene Related Peptide fragment 8–37
Calcitonin Precursor Peptide
Calmodulin-Dependent Protein Kinase II (fragment 290–309)
Calpain Inhibitor I
Calpain Inhibitor II
Calpain Inhibitor Peptide
Carassin
N-Carboxymethyl-Phe-Leu
N-([R.S]-2-Carboxy-3-phenylpropionyl)-L-Leucine
Cardioexcitatory Peptide
alpha-Casein and fragments
Beta-Casomorphin
Nα-CBZ-Arg-Arg-Pro-Phe-His-Sta-Ile-His-Nε-BOC-Lys Methyl Ester
CBZ-Leu-Val-Gly Diazomethyl Ketone
N-CBZ-D-Phe-Phe-Gly
N-CBZ-Pro-D-Leu
N-CBZ-Pro-Leu-Gly Hydroxamate
CD4 and fragments
Cecropins
Cerebellin
Chemostactic Peptides
Cholecystokinin and fragments
Chorionic Gonadotropin and fragments
Chromostatin-20
Chymostatin
Circumsporozoite (CS) Protein of Plasmodium falciparum repetitive sequences
Collagen
Conotoxin GI
μ-conotoxin GIIIB
ω-conotoxin GVIA
α-conotoxin SI
Copper Binding Peptide
Corazonin
Corticotropin A
Corticotropin-Like Intermediate Lobe Peptide
Corticotropin Releasing Factor and analogs
Tyr-Corticotropin Releasing Factor
Corticotropin Releasing Factor Antagonist
C-Peptide and fragments
Cyclic-AMP Dependent Protein Kinase Substrate
Cyclo(7-Aminoheptanoyl-Phe-D-Trp-Lys-Thr[Bzl])
Cyclo(D-Asp-Pro-D-Val-Leu-D-Trp)
Cyclohexylacetyl-Phe-Arg-Ser-Val-Gln Amide
Cyclo(His-Phe)

Cyclo(His-Pro)
Cyclo(Leu-Gly)
Cyclo(Phe-Ser)
Cyclo(Pro-Gly)3
Cyclo(D-Trp-Lys-Thr-Phe-Pro-Phe)
Cyclo(D-Trp-Lys-Thr-Phe-Pro-Tyr)
Cys-Gin-Asp-Ser-Glu-Thr-Arg-Thr-Phe-Tyr
Cys-Ser-Arg-Ala-Arg-Lys-Gln-Ala-Ala-Ser-Ile-Lys-Val-Ala-Val-Ser-Ala-Asp-Arg
Cys-Tyr-Ile-Gln-Asn-Cys-Pro-Arg-Gly Amide
Cys-Tyr-Ile-Gin-Asn-Cys-Pro-Leu Gly Amide
Cys-Tyr-Ile-Ser-Asn-Cys-Pro-Ile-Gly Amide
DAGO (D-Ala2, N-Me-Phe4-Gly5-ol-Enkephalin)
Dalargin
Decorin
Delta Sleep Inducing Peptide
Dermenkephalin
Dermorphin
Diabetes Associated Peptide Amide
Diazepam Binding Inhibitor and fragments
Diprotin A
Diprotin B
DNA Binding Peptide
Dynorphin and fragments
Echistatin
Elastatinal
Elastin Chemotactic protein and fragment
Eledoisin
Eledoisin-Related Peptide
Endothelin
alpha-Endorphin
beta-Endorphin and fragments
gamma-Endorphin
Endothelins
Enkephalin, Leucine and analogs
Enkephalinamide, Leucine and analogs
Enkephalin, Methionine and analogs
Enkephalinamide, Methionine and analogs
Enzyme Inhibitors
Eosinophilotactic Tetrapeptides
Epiamastatin
Epibestatin
Epidermal Growth Factor
Epidermal Mitosis Inhibiting Pentapeptide
Experimental Allergic Encephalogenic Peptide
Erythropoietin fragment 1–26
Fibrinogen-Binding Inhibitor Peptide
Fibrinogen Related Peptide
Fibrinogen A and analogs
Fibrinogen B and analogs
Fibroblast Growth Factor, Acidic fragment 1–11
Fibroblast Growth Factor, Basic fragment 1–24
Fibronectin-Binding Protein Peptide D3
Fibronectin fragments and analogs
Fibronectin Related Peptide
Fibronectin Pepsin (e.g. 50K)
Fibronectin Chymotrypsin (e.g. 40K, 45K, 120K)
Fibronectin Trypsin (e.g. 30K, 60K)
N-FMOC-val-Gly-Gly-O-t-Butyl-Tyr-Gly-O-t-Butyl-Tyr-Gly-Ala-Ne-CBZ-Lys
N-Formyl-Met-Leu-Phe
Formyl-Peptides
Foroxymithine
FTS (Serum Thymic Factor)
Galanin Message Associated Peptide and fragments
Galanin
Gastric Inhibitory Polypeptide
Gastrin I and fragments
Gastrin I, Big
Gastrin II
Pentagastrin
Gastrin Releasing Peptide
Gastrin-Tetrapeptide Amide
Gastrointestinal Peptides
Gilodeliquescin
Gin-Ala-Thr-Val-Gly-Asp-Ile-Asn-Thr-Glu-Arg-Pro-Gly-Met-Leu-Asp-Phe-Thr-Gly-Lys
Gln-AJa-Thr-Val-Gly-Asp-Val-Asn-Thr-Asp-Arg-Pro-Gly-Leu-Leu-Asp-Leu-Lys
Gln-Arg-Arg-Gln-Arg-Lys-Ser-Arg-Arg-Thr-Ile
Gln-Lys-Arg-Pro-Ser-Gln-Arg-Ser-Lys-Tyr-Leu
Glu-Ala-Glu
Glu-Ala-Glu-Asn
Glucagon
Glucagon(1–37)
Glucagon-Like Peptide I and fragments
Glu-Leu-Ala-Gly-Ala-Pro-Pro-Glu-Pro-Ala
Glutathione and analogs
Gly-Arg-Ala-Asp-Ser-Pro
Gly-Arg-Ada-Asp-Ser-Pro-Lys
Gly-Arg-Gly-Asp
Gly-Arg-Gly-Asp-Asn-Pro
Gly-Arg-Gly-Asp-Ser
Gly-Arg-Gly-Asp-Ser-Pro
Gly-Arg-Gly-Asp-Ser-Pro-Lys
Gly-Arg-Gly-Asp-Thr-Pro
Gly-Arg-Gly-Leu-Ser-Leu-Ser-Arg
Gly-Arg-Tyr-Asp-Ser
Gly-Gln
Gly-Glu-Gln-Arg-Lys-Asp-Val-Tyr-Val-Gin-Leu-Tyr-Leu
Gly-Gly-Arg
Gly-Gly-His
Gly-Gly-Tyr-Arg
Gly-His-Arg-Pro
Gly-His-Lys
Gly-Leu-Met Amide
Gly-Pen-Gly-Arg-Gly-Asp-Ser-Pro-Cys-Ala(Pen2,Cys9 cyclic)
Gly-Phe-Asp-Leu-Asn-Gly-Gly-Gly-Val-Gly
Gly-Pro-Arg
Gly-Pro-Arg-Pro
Gly-Pro-Gly-Gly
Granuliberin R Granulocyte Macrophage-Colony Stimulating Factor
GRF 1–40, Human
Growth Hormone Release Inhibiting Factor
Growth Hormone Releasing Factor and fragments
H-142
Helodermin
Hepatitis A viral proteins and peptides
Hepatitis B Virus Pre-S Region (120–145)
Hepatitis C Viral proteins and peptides
Herpes Virus Ribonucleotide Reductase Inhibitors
Heterotypic Adhesion Receptor
Hirudin and fragments
His-Asp-Met-Asn-Lys-Val-Leu-Asp-Leu
His-Leu-Gly-Leu-Ala-Arg
His-Lys-Ala-Arg-Val-Leu-p-Nitro-Phe-Glu-Ala-Nle-Ser Amide
D-His-Pro-Phe-His-Leu-ph-[CH$_2$NH]-Leu-Val-Tyr
Histories
HIV Envelope Protein (gp41) fragment 579–601
HIV Envelope Protein (gp120) fragments
HIV Protease Inhibitor
HIV Substrate, III
HIV vital protein and peptides
Histone H2A fragment 86–120
Hydra Peptide and fragments
Hypercalcemia Malignancy Factor –40
Hypertrehalosaemic Neuropeptide
Iberiotoxin
Ile-Pro-Ile
Ile-Val-Pro-Phe-Leu-Gly-Pro-Leu-Leu-Gly Leu-Leu-Thr Amide
Immunostimulating Peptides
Inhibin, alpha subunit, fragment 1–32
Insulin Chain A, oxidized
Insulin Chain B, oxidized
Insulin Chain B fragment 22–30
Insulin Chain C
Insulin-Like Growth Factor I
Insulin-Like Growth Factor II
Integrin (e.g. alpha 4, alpha V beta 5 alpha2, alpha3, alpha 5, alpha V, beta 1, beta 2, beta 4)
Interleukin 1B fragment (163–171)
Interleukin-2 Receptor C-Terminal Sequence
Interleukin (e.g. 1 alpha, 2, 6, gamma)
Isotocin
Kallidin
Kallikrein Inhibitor
Kassinin
Katacalcin and analogs
Kemptide and analogs
Kentsin
Kinetensin
Kyotorphin and analogs
Laminin and fragments (929–933)
Leu-Arg-Arg-Ala-Ser-Leu-Gly
Leu-Arg-Arg-Ala-Hse-Leu-Gly
Leu-Arg-Arg-Trp-Ser-Leu-Gly
Leucokinins
Leucopyrokinin and fragments
Leu-Leu Methyl Ester
Leu-Lys-Lys-Phe-Asn-Ala-Arg-Arg-Lys-Leu-Lys-Gly-Ala-Ile-Leu-Thr-Met-Leu-Ala
Leu-Pro-Pro-Ser-Arg
Leu-Ser-(pNO2)-Phe-Nle-Ala-Leu Methyl Ester
Leupeptin
LH-RH (Luteinizing Hormone Releasing Hormone) and analogs
beta-Lipotropin and fragments
Litorin
Lys-Arg-Pro-Pro-Gly-Phe-Ser-Pro-Phe-Arg
Lys-Ala-Arg-Val-Nle-p-Nitro-Phe-Glu-Ala-Nle Amide
Lys-Arg-Thr-Leu-Arg-Arg
Lys-Cys-Thr-Cys-Cys-Ala
Lys-Glu-Glu-Ala-Glu
Lys-His-Gly Amide
Lys-Lys-Arg-Ala-Ala-Arg-Ala-Thr-Ser-Amide
Lys-Lys-Asp-Ser-Gly-Pro-Tyr
Lys-Lys-Gly-Glu
Lys-Phe-Ile-Gly-Leu-Met Amide
Lys-Pro-Pro-Thr-Pro-Pro-Pro-Glu-Pro-Glu-Thr
Lys-Trp-Lys
D-Lys-Tyr-D-Trp-D-Trp-Phe
D-Magainin II Amide
Magainin I
Magainin II
Manning Compound
Manning-Binding Protein
Mast Cell Degranulating Peptide
Mast Cell Degranulating Peptide HR1
Mast Cell Degranulating Peptide HR2
Mastoparan
Alpha1-Mating Factor
MCD Peptide
MB-35
Alpha-Melanocyte Stimulating Hormone and analogs
Beta-Melanocyte Stimulating Hormone
Delta-Melanocyte Stimulating Hormone
Melittin
Merosin
Met-Asn-Tyr-Leu-Ala-Phe-Pro-Arg-Met Amide
Met-Gln-Met-Lys-Lys-Val-Leu-Asp-Ser
Met-Gly-Trp-Asn-Ser-Thr-Thr-Phe-His-Gin-Thr-Leu-Gln-Asp-Pro-Arg-Val-Arg-Gly-Leu-Tyr-Phe-Pro-Ala-Gly-Gly
Met-Leu-Phe
Metorphamide
Molluscan Cardioexcitatory Peptide
Morphiceptin
Morphine Modulating Neuropeptide
Morphine Tolerance Peptide
Motilin
MSH
Muramyl Dipeptides
Beta-Naphthyl-D-Ala-Cys-Tyr-D-Trp-Lys-Val-Cys-Thr Amide coendorphin
Beta-Neoendorphin
Alpha-Neurokinin
(Ala5, Beta-Ala8)-alpha-Neurokinin fragment 4–10
Neurokinin (e.g., A, Nle-10, B, MePhe7-B)
Neuromedins (e.g., B,C)
Neuropeptide K
Neuropeptide Y
Neurotensin and analogs
N-Nicotinoyl-Tyr-(Nalpha-CBZ-Arg)-Lys-His-Pro-Ile
Nle-Arg-Phe Amide
Nle-Sta-Ala-Sta
NeutrAvidin
Octadecaneuropeptide (e.g. 6, 7, 8)
Osteocalcin fragment 7–19
Osteocalcin fragment 45–49
Oxyntomodulin
Oxytocin and analogs
PACAP27 Amide
Pancreastatin and fragments
Pancreatic Polypeptide
Parathyroid Hormone and fragments
Pardaxin
Pentagastrin
Pepstatin A
Peptide II of T. wagleri Venom
Peptide T
Peptide YY
pGlu-Ala-Glu
pGlu-Ala-Lys-Ser-Glu-Gly-Gly-Ser-Asn
pGlu-Asn-Gly
pGlu-Asp-Pro-Phe-Leu-Arg-Phe Amide
pGlu-Gln-Arg-Leu-Gly-Asn-Gln-Trp-AJa-Val-Gly-His-Leu-Met Amide
pGlu-Gln-Asp-Tyr(SO3H)-Thr-Gly-Trp-Met-Asp-Phe Amide
pGlu-Glu-Asp-Ser-Gly
pGlu-Gly-Leu-Pro-Pro-Arg-Pro-Lys-Ile-Pro-Pro
pGlu-Gly-Leu-Pro-Pro-Gly-Pro-Pro-Ile-Pro-Pro
pGlu-His-Gly
pGlu-His-Gly Amide
pGlu-His-Pro
pGlu-His-Pro Amide
pGlu-His-Pro-Gly
pGlu-His-Trp-Ser-Tyr-Gly-Leu-Arg-Pro-Gly Amide
pGlu-Leu-Tyr-Glu-Asn-Lys-Pro-Arg-Arg-Pro-Tyr-Ile-Leu
pGlu-Lys-Arg-Pro-Ser-Gln-Arg-Ser-Lys-Tyr-Leu
pGlu-3-Methyl-His-Pro Amide
(pGlu4)-Myelin Basic Protein 4–14
pGlu-Ser-Leu-Arg-Trp Amide
pGlu-Thr-Ser-Phe-Thr-Pro-Arg-Leu Amide
pGlu-Trp-Pro-Arg-Pro-Gln-Ile-Pro-Pro
pGlu-Val-Asn-Phe-Ser-Pro-Gly-Trp-Gly-Thr Amide
Paracelsin
Peptide 6a
[D-Ala1]-peptide T amide
Phe-Gly-Gly-Phe
Phe-Gly-Leu-Met Amide
Phe-Gly-Phe-Gly
Phe-Leu-Arg-Phe Amide
Phe-Leu-Glu-Glu-Ile
Phe-Leu-Glu-Glu-Leu
Phe-Leu-Glu-Glu-Val
Phe-Leu-Phe-Gln-Pro-Gln-Arg-Phe Amide
Phe-Met-Arg-Phe Amide
Phe-Met-Arg-D-Phe Amide
Phe-Met-D-Arg-Phe Anude
Phe-D-Met-Arg-Phe Amide
D-Phe-Met-Arg-Phe Amide
Phe-Ser-Trp-Gly-Ala-Glu-Gly-Gln-Arg
PHI
Phosphoramidon
Phosphate Acceptor Peptides
(Val6, Ala7)-Kemptide
Physalaemin
Platelet Derived Growth Factor (AB-chain, heterodimer, AA homodimer, BB homodimer)
Platelet Membrane Glycoprotein IIB Peptide
Pre-Pro-Gonadotropin Releasing Hormone fragment 14–26
Pressinoic Acid
N-proCalcitonin 1–57
Proctolin
Prodynorphin 228–240
Proenkephalin
Pro-His-Pro-Phe-His-Phe-Phe-Val-Tyr-Lys
Pro-Leu-Gly Amide
Pro-Phe-Gly-Lys
Pro-Leu-Ser-Arg-Thr-Leu-Ser-Val-Ala-Ala-Lys-Lys
Prosomatostatin 1–32
PYY
Protected Marine Adhesive Peptide
Protein A
Protein G (binds to Fc region, specially of IgG1 subclass)
Protein Kinase C
Protein Kinase C Substrate
Protein Kinase Inhibitor
Pro-Thr-Pro-Ser Amide
PTH
PTH-Related Protein (1–40)
Ranatensin
Renin Inhibitors
Renin Substrate Tetradecapeptide
N-(alpha-Rhamnopyranosyloxyhydroxyphosphinyl)-Leu-Trp
Sarafotoxin
Schizophrenia Related Peptide
Secretin
Senktide
Ser-Asp-Gly-Arg-Gly
Ser-Gln-Asn-Phe-Phi($CH_2N$)-Pro-Ile-Val-Gln
Ser-Gin-Asn-Tyr-Pro-Ile-Val
Ser-Ile-Gly-Ser-Leu-Ala-Lys Ser-Phe-Leu-Leu-Arg-Asn-Pro-Asn-Asp-Lys-Tyr-Glu-Pro-Phe
Serglycin
Serum Thymic Factor and analogs
Sexual Agglutination Peptide
Sleep Inducing Peptide
Small Cardioactive Peptide B
Somatostatin and analogs
Speract
Streptavidin
Streptolysin
Substance P and analogs
SV40 Tumor Antigen C-Terminal Sequence
Syndyphalin
Syntide
Tenascin
Terlipressin
Thapsigargin
DL-Thiorphan
Thr-Lys-Pro-Arg
Thrombin Receptor Activator
Thr-Phe-Gln-Ala-Tyr-Pro-Leu-Arg-Glu-Ala
Thr-Pro-Arg-Lys
Thr-Ser-Lys
Thr-Thr-Tyr-Ala-Asp-Phe-Ile-Ala-Ser-Gly-Arg-Thr-Gly-Arg-Arg-Asn-Ala-Ile-His-Asp
Thr-Tyr-Ser
Thr-Val-Leu
Thrombospondin
Thymopoietin fragments
Thymosin
Thymosin fragments
Thyrocalcitonin
Thyrotropin Releasing Hormone and Related Peptides
Tocinoic Acid
Toxin, Snake
TP-5
Transforming Growth Factor-Alpha
TRH
Trp-Ala-Gly-Gly-Asp-Ala-Ser-Gly-Glu
D-Trp-Ala-Trp-D-Phe Amide
Trp-His-Trp-Leu-Gln-Leu
Trp-His-Trp-Leu-Gln-Leu-Lys-Pro-Gly-Gln-Pro-Met-Tyr
Trp-His-Trp-Leu-Ser-Phe-Ser-Lys-Gly-Glu-Pro-Met-Tyr
Trp-Met-Asp-Phe Amide
Trp-Nle-Arg-Phe Amide
Tuftsin and analogs
Tumor Necrosis factor (e.g. alpha) Tyr-Ala-Gly-Ala-Val-Val-Asn-Asp-Leu
Tyr-D-Ala-Phe-Asp-Val-Val-Gly Amide
Tyr-D-Ala-Phe-Glu-Val-Val-Gly Amide
Tyr-Gly-Ala-Val-Val-Asn-Asp-Leu
Tyrosine Protein Kinase Substrate
Tyr-D-Ala-Gly
Tyr-Gly-Gly
Tyr-D-Ala-Phe-Met Amide
Tyr-Arg
Tyr-Gly-Gly
Tyr-Gly-Gly-Phe-Leu
Tyr-Gly-Gly-Phe-Leu-Arg-Arg-Ile-Arg-Pro-Arg-Leu-Arg-Gly-Aminopentylamide
Tyr-Gly-Gly-Phe-Met-Arg-Arg-Val
Tyr-Gly-Gly-Phe-Met-Arg-Arg-Val Amide
Tyr-Gly-Gly-Phe-Met-Arg-Gly-Leu
Tyr-Gly-D-Trp-Phe-D-Phe Amide
Tyr-Ile-Gly-Ser-Arg
Tyr-Phe-Met-Arg-Phe Amide
Tyr-Pro-Leu-Gly Amide
Tyr-Pro-Phe-Pro Amide
Tyr-Pro-Val-Pro Amide
Tyr-D-Ser-Gly-Phe-Leu-Thr
Tyr-D-Trp-Ala-Trp-D-Phe Amide
Tyr-D-Trp-Ala-Trp-D-Phe Methyl Amide
Urodilatin
Urotensin I
Urotensin II
Val-Ala-Ala-Phe
Val-Arg-Lys-Arg-Thr-Leu-Arg-Arg-Leu
Val-Glu-Glu-Ala-Glu
Val-Glu-Pro-Ile-Pro-Tyr
Val-Glu-Ser-Ser-Lys
Val-Gly-Asp-Glu
Val-Gly-Ser-Glu
Val-Gly-Val-Ala-Pro-Gly
Val-His-Leu-Thr-Pro
Val-His-Leu-Thr-Pro-Val-Glu-Lys
Val-Ile-His-Asn
Valosin
Val-Pro-Leu
Vasoactive Intestinal contractor
Vasoactive Intestinal Peptide and analogs
Vasopressin and analogs
Vasotocin
Versican
Vitronectin
Xenopsin
Yeast Alpha-Factor
Human serum albumin glycoconjugates:
  Carboxyethylthioethyl 2-Acetamido-2-deoxy-3-O-Beta-D-galactopyranosyl-beta-D-glucopyranoside-HSA Conjugate
  Carboxyethylthioethyl 2-Acetamido-2-deoxy-4-O-beta-D-galactopyranosyl-beta-D-glucopyranoside-HSA Conjugate
  Carboxyethylthioethyl 2-Acetamido-4-O-(2-acetamido-2-deoxy-beta-D-glucopyranosyl-6-O-(alpha-L-fucopyranosyl))-2-deoxy-beta-D-glucopyranoside-HSA Conjugate
  Carboxyethylthioethyl 4-O-alpha-D-Galactopyranosyl-beta-D-galactopyranoside-HSA Conjugate
  Carboxyethylthioethyl 4-O-(4-O-(6-O-alpha-D-Glucopyranosyl-alpha-D-glucopyranosyl)-alpha-D-glucopyranosyl)-beta-D-glucopyranoside-HSA Conjugate Free oligosaccharides and simple derivatives:
- 2-Acetamido-6-O-(2-acetamido-2-deoxy-beta-D-glucopyranosyl)-2-deoxy-D-glucopyranose
- 2-Acetamido-2-deoxy-3-O-beta-D-galactopyranosyl-D-galactopyranose
- 2-Acetamido-2-deoxy-4-O-(4-O-Beta-D-galactopyranosyl-beta-D-galactopyranosyl)-D-glucopyranose
- 2-Acetamido-2-deoxy-3-O-beta-D-galactopyranosyl-D-glucopyranose
- 2-Acetamido-2-deoxy-6-O-beta-D-galactopyranosyl-D-glucopyranose
- 6-O-(2-Acetamido-2-deoxy-4-O-(beta-D-galactopyranosyl)-beta-D-glucopyranosyl)-D-galactopyranose
- 6-O-(2-Acetamido-2-deoxy-beta-D-glucopyranosyl)-D-galactopyranose
- 4-O-(6-O-(2-Acetamido-2-deoxy-beta-D-glucopyranosyl)-beta-D-galactopyranosyl)-D-glucopyranose
- N-Acetyllactosamine
- Benzyl 2-Acetamido-6-O-(2-acetamido-2-deoxy-beta-D-glucopyranosyl)-2-deoxy-alpha-D-glucopyranoside
- Benzyl 2-Acetamido-2-deoxy-3-O-beta-D-galactopyranosyl-alpha-D-galactopyranoside
- Benzyl 2-Acetamido-2-deoxy-3-O-beta-D-galactopyranosyl-beta-D-glucopyranoside
- Benzyl 4-O-beta-D-Galactopyranosyl-beta-D-glucopyranoside
- n-Butyl 4-O-beta-D-Galactopyranosyl-beta-D-glucopyranoside
- D-(+)-Cellobiose
- D-(+)-Cellopentaose
- D-(+)-Cellotetraose
- D-(+)-Cellotriose
- Digalacturonic acid
- Ethyl 2-Acetamido-2-deoxy-4-O-(4-O-alpha-D-galactopyranosyl-beta-D-galactopyranosyl)-beta-D-glucopyranoside
- Ethyl 4-O-beta-D-Galactopyranosyl-beta-D-glucopyranoside
- 2'-Fucosyllactose
- 3-Fucosyllactose
- 4-O-alpha-D-Galactopyranosyl-D-galactopyranose
- 6-O-beta-D-Galactopyranosyl-D-galactopyranose
- 4-O-(4-O-beta-D-Galactopyranosyl-beta-D-galactopyranosyl)-D-Glucopyranose
- 4-O-beta-D-Galactopyranosyl-D-mannopyranose
- 4-O-(4-O-(6-O-alpha-D-Glucopyranosyl-alpha-D-glucopyranosyl)alpha-D-glucopyranosyl)-D-glucopyranose
- Lacto-N-tetraose
- 3-O-alpha-D-Mannopyranosyl-D-mannopyranose
- Methyl 4-O-(3-O-(2-Acetamido-2-deoxy-4-O-beta-D-galactopyranosyl-beta-D-glucopyranosyl)-beta-D-galactopyranosyl)-beta-D-glucopyranoside
- Methyl 3-O-(2-Acetamido-2-deoxy-beta-D-glucopyranosyl)-beta-D-galactopyranoside
- Methyl 6-O-(2-Acetamido-2-deoxy-beta-D-glucopyranosyl)-alpha-D-mannopyranoside
- Methyl 3,6-Di-O-(alpha-D-mannopyranosyl)-alpha-D-mannopyranoside
- Methyl 3-O-beta-D-Galactopyranosyl-beta-D-galactopyranoside
- 4-O-(2-O-Methyl-beta-D-galactopyranosy)-D-glucopyranose
- Methyl 4-O-beta-D-Galactopyranosyl-beta-D-glucopyranoside
- Methyl 2-O-alpha-D-Mannopyranosyl-alpha-D-mannopyranoside
- Methyl 3-O-alpha-D-Mannopyranosyl-alpha-D-mannopyranoside
- Methyl 4-O-alpha-D-Mannopyranosyl-alpha-D-mannopyranoside
- Methyl 6-O-alpha-D-Mannopyranosyl-alpha-D-mannopyranoside
- n-Propyl 4-O-beta-D-Galactopyranosyl-beta-D-glucopyranoside
- Trigalacturonic acid Activated oligosaccharides:
- Carbomethoxyethylthioethyl 2-Acetamido-2-deoxy-4-O-beta-D-galactopyranosyl-beta-D-glucopyranoside
- Carbomethoxyethylthioethyl 4-O-(4-O-(6-O-alpha-D-Glucopyranosyl-alpha-D-glucopyranosyl)-alpha-D-glucopyranosyl)-beta-D-glucopyranoside
- p-Nitrophenyl 2-Acetamido-2-deoxy-3-O-(2-acetamido-2-deoxy-beta-D-glucopyranosyl)-alpha-D-galactopyranoside
- p-Nitrophenyl 2-Acetamido-2-deoxy-3-O-(Beta-D-galactopyranosyl)-alpha-D-galactopyranoside
- p-Nitrophenyl 2-Acetamido-2-deoxy-3-O-beta-D-galactopyranosyl-beta-D-glucopyranoside
- p-Nitrophenyl 6-O-beta-D-galactopyranosyl-beta-D-galactopyranoside
- p-Nitrophenyl alpha-D-Maltopentaoside Neo-glycolipids:
- Octadecylthioethyl 4-O-alpha-D-Galactopyranosyl-beta-D-galactopyranoside
- Octadecylthioethyl 4-O-(4-O-(6-O-alpha-D-Glucopyranosyl-alpha-D-glucopyranosyl)-alpha-D-glucopyranosyl)-beta-D-glucopyranoside Coagulation proteins and various factors, and their fragments, inhibitors, receptors to which they bind, or genes and information molecules from which they may be derived:
   Acutase; Agkistrodon contortrix Thrombin-like Enzyme; Ancrod; α2-Antiplasmin; Antithrombin III; Atroxin; Coagulation Factors; Coagulation factor Inhibitors; Crotalase; Ecarin; Factor I, II, III, IV, V; Factor V Activating Enzyme; Factor VI, VII; VIII; Von-Willebrand Factor; Factor IX; Factor X; Factor X, Activiated (Xa) Factor X Activating Enzyme; Factor XI, XII, XIII; Fibrin; Fibrin/Fibrinogen Degradation products; Fibrinogen; Fibrinolytic proteins; Heparin; Hirudin; Kallikrein; Plasmin; Plasminogen; Plasminogen Lysine Binding Sites; Platelet Factor 4; Platelet Aggregation Reagent; Brain Cephalin; Snake venoms; Streptokinase; Thrombins; Thromboplastin; Thromboplastin with Calcium; Tissue Plasminogen Activator; Urokinase Agents and drugs used to treat or prevent HIV infection:
   Alpha interferon, Interleukin-2, Amphotericin B, Amphotericin B Methyl Est; Ampligen (polyI-polyC; C12U); AS-101 (ammonium trichloro (dioxyethylene-O-O' tellurate); CD8+ lymphycyte proteins; HIV viral proteins, cell receptor anagonists, cell receptor binding proteins; azidothymidine and analogs or conjugates;

Azidouridine (including analogs or conjugates); beta interferon; Carbovir; Carrisyn; Colchicine; Colony Stimulating Factors; Compound Q; D4T (2',3'-didehydro-3'-dideoxythymidine); DTC (Imuthiol); Dextran Sulfate; Dideoxycytidine; Dideoxyinosine; DHEA (dehydroepiandro-sterone); Doxorubicin; gamma globulin; HIV-immunogen; Hypericin; tyrosine-glycine dipeptide; tyrosine-glycine-glycine tripeptide; Isoprinosine; Lentinan (beta-(1–3)-glucan); Lipid compounds, e.g. AL-721 or EL-721 and like products; Peptide T; Polio Vaccine proteins; soluble CD4; CD4-linked toxins; Ribavirin; SMS 201–995 (a long-acting analog of somatostatin); Thymic Humoral Factor; Thymopentin; Tumor Necrosis Factor; ketoconazole; fluconazole; Eflornithine; Spiramycin; Ganciclovir (DHPG); Foscarnet; Acyclovir; Vibaradine; Pyrimethamine; sulfadiazine; TMP/SMX; Amikacin; Ansamycin; Ciprofloxacin; Clofazamine; Cycloserine; Imipenum; Ethambutol; Isoniazide; Rifampin; Streptomycin; sulfa based antibiotics; pentamidine; Dapsone/ trimethoprim; steroids; Trimetrexate with Leukovorin; Clindamycin; primaquin; Dapasone; Spiramycin; piritrexim Adjuvant peptides:

N-acetylmuramyl-L-alanyl-D-isoglutamine

N-acetylmuramyl-D-alanyl-D-isoglutamine

N-acetylmuramyl-L-alanyl-L-isoglutamine

N-acetylmuramyl-L-alanyl-D-isoglutamine-6-O-stearoyl

N-acetyl-glucosaminyl-beta(1–4)-N-acetylmuramyl-L-alanyl-D-isoglutamine

Components of Freund's Complete Adjuvant

Components of Freund's Incomplete Adjuvant

Dimethyldioctyldecyl Ammonium Bromide

Lipoproteins and related enzymes:

Apolipoprotein A (I and II), B, CIII, CII, CI, E

High Density Lipoprotein

Low Density Lipoprotein

Very Low Density Lipoprotein

Lipoprotein Lipase

Lipoteichoic Acid

Lipoxidase

Diaphorase

Lipoxin A4, B4

Lipoxygenase

Prostaglandan Synthetase

Chelating agents:

Iminodiacetic Acid (e.g., dimethyl-ida, paraisopropyl-ida, parabutyl-ida, diisopropyl-ida, diethyl-ida)

EDTA (Ethylenediaminetetraacetic acid)

NTA (Nitriloacetic acid)

TPP (Tripolyphosphate

Cysteine

DEDTC (Diethyldithiocarbamate)

Citric acid

Tartaric acid

Penicillamine

EGTA

Caged calcium chelators:

NITR5, NITR7, DM-nitrophen, NITR5/AM; Ammonium N-nitrosophenyl-hydroxylamine; Ammonium purpurate; alpha-Benzoin oxime; N,N-Bis-(hydroxyethyl)-glycine; 2,3-butane-dione dioxime; Trans-1,2-Diaminocyclo-hexanetetra-acetic acid (CDTA); Diethylene-triaminopenta-acetic acid (DTPA); 4,5-Dihydroxy-benzene-1,3-disulphonic acid; 2,3-Dimercapto-Propanol; Diphenylthio-carbazone; 2,2'-Dipyridyl; 3,6-Disulpho-1,8-dihydroxy-naphthalene; Dithiooxamide; Eriochrome Black T; Ethylenediamine; Ethylenediaminetetraacetic acid (EDTA); (Ethylene-dioxy)-diethylenedinitrilo-tetraacetic acid (EGTA); o-Hydroxybenzaldehyde oxime; N-(2'-Hydroxyethyl)iminodiacetic acid (HIMDA); 8-Hydroxy-quinoline; Hydroxyquinoline-5-sulphonic acid; 4-Methyl-1,2-dimercapto-benzene; Nitrilotriacetic acid (NTA); 5-Nitro-1,10-phenanthroline; 1,10-Phenanthroline; Potassium ethyl xanthate; Salicylic acid; sodium diethyldithio-carbamate; 2-Thenoyl-2-furoylmethane; Thenoyl-trifluoro-acetone; Thiourea; Triethylenetetramine Deferoxamine mesylate Edetate Calcium disodium meso 2,3-dimercapto succinic acid Penicillamine Trientine Chelators specially useful in chelating Tc99m:

A thiolactone diaminedithiol bifunctional chelating agent p-carboxyethylphenylglyoxal-di-N-methylthioxemicrobazone A diamide dimercaptide chelating agent A hydroxy compound (e.g. cyclohexanol) attached to cysteine Bisthio semicarbazones Cyclan Diamido dithio ligands Radionuclides:

Indium 111

Thallium 201

Technetium 99m

Other compounds and chelates suitable for MRI imaging:

Gadolinium, Cadmium, Strontium, Chromium; ferrous gluconate; manganese; nickel, piperidine and pyrrolidine NSFR derivatives, ferric ammonium citrate Reagents that can be used to provide spacer arms for bioreactive molecules to extend beyond the immediate surface of the particles:

Biocytin

Biocytin hydrazide p-Aminobenzoyl Biocytin

Enzymes:

Alteplase; Anistreplase; Adenosine Deaminase; Amylase; Angiotensin I, II, III; Calmodulin; Carboxypeptidase; Catalase; Cellulase; Cholesterol oxidase; Cholinesterase; Chymotrypsin; Collagenase; Complement cascade proteins; Creatine phosphokinase; Deoxyribonuclease I, II; Dipeptidyl peptidase; DNA polymerase; Endoproteinase; Endonucleases; Esterases; beta-Galacatosidase; Galactose oxidase; Galactose dehydrogenase; Glucose dehydrogenase; Glucose oxidase; Glucose-6-phosphate dehydrogenase; Glucuronidase/ Aryl sulfatase; Glutamate-oxaloacetate transaminase; Glutamate-pyruvate transaminase; Glutathione reductase; Glutathione peroxidase; Glycopeptidase; Hementin; Hemoglobin; Hexokinase; Hyaluronidase; Lactate dehydrogenase; Lactoperoxidase; Lactamase; Lipase;

Myokinase; Neuraminidase; Nicotinamide-adenine Dinucleotide kinase; Nicotinamide-adenine Dinucleotide oxidase; Nuclease; Nucleosidase; Papain; Peroxidase; Phenylalanine dehydrogenase; phosphatase (acid or alkaline); Phosphodiesterase; Phospholipase (A2, C, D); Plasmin; Proteases; Protein Kinase C; Proteinase K; Renin; Reverse transcriptase; Ribonuclease (A, T1, T2, U2); RNA polymerase; Sialytransferase; Streptokinase; Subtilisin A; Superoxide dismutase; Terminal transferase; Urease; Urokinase Nucleotides and fragments thereof:
  anti-sense (DNA or RNA against RNA or DNA, single or double stranded), cloning vectors, coliphage DNA, lambda phage DNA, M13 DNA, Adenovirus DNA, phi-X 174 phage DNA, Simian virus DNA, cytomegalovirus DNA, Epstein-Barr Virus genes, Herpes Simplex genes, ribosomal RNA, human DNA and RNA; Genes coding for ribozymes; genes coding for antibiotics (e.g., ampicillin, chloramphenicol, cycloserine, gentamycin, kanamycin, kasugamycin, nalidixic acid, rifampicin, spectinomycin, streptomycin, tetracycline)

Platelet related proteins and enzymes:
  Platelet factor 4; 1-3-Dioxolane; 1-O-Hexadecyl-2-acetyl-sn-glucero-3-phospho-(N,N,N-trimethyl)-hexanolamine; Platelet activating factors (e.g., 1-O-hexadecyl-2-acetyl-sn-glycero-3-phosphocholine; 3-O-hexadecyl-2-acetyl-sn-glycero-1-phosphocholine; 1-O-hexadecyl-sn-glycero-3-phosphocholine; 1-O-hexadecyl-2-N-methylcarbamyl-sn-glycero-3-phosphocholine; 1-O-hexadecyl-2-thioacetyl-2-deoxy-sn-glycero-3-phosphocholine; 1-O-hexadecyl-2-acetyl-sn-glycero-3-phospho(N-methylpyrrolidino)-ethanolamine); Platelet activating factor 18; 18:1; Lyso-platelet activating factor 18; platelet activating factor-16; Enantic-platelet activating factor-16; Lyso-platelet activating factor-16; trans-2,5-bis-(3,4,5-trimethoxyphenyl); 1-O-Hexadecyl-2-acetyl-sn-glycero-3-phospho(N,N,N-trimethyl)-hexanolamine.

Other compounds:
  Protein A,B,C,G,S; Ricin A; Proadifen (SKF-525A)1 Taxol; Thiolytes; Thiostrepton; Thrombin Thrombocytin; beta-Thromboglobulin; Thrombospondin; Transferrin (apo-, partial iron, holo); Tumor Necrosis factor; Vitronectin, Forskolin, Integrins; caged compounds (caged ATP, caged INsP3, caged cAMP, caged cGMP, caged GTP, caged carbamoyl chorine); Mezerein; Plasminogen; Aminocaproic acid; desmopressin acetate; Activase RGD-containing peptides:
  Gly-Arg-Gly-Asp-Ser-Pro
  Gly-Arg-Gly-Asp-Thr-Pro
  Gly-Arg-Gly-Asp-D-Ser-Pro
  Gly-D-Arg-Gly-Asp-Ser-Pro
  Gly-Arg-Gly-Glu-Ser-Pro (inactive control peptide)
  Gly-Arg-Gly-Asp-Asn-Pro
  n-Methyl-Gly-Arg-Gly-Asp-Ser-Pro
  Arg-Gly-Asp-Ser
  Gly-Arg-Gly-Asp-Ser
  Gly-Arg-Gly-Asp-Ser-Pro-Cys
  Gly-Arg-Gly-Asp-Ser-Pro-Lys
  Gly-Arg-Gly-Asp-Ser-Pro-Ala-Ser-Ser-Lys
  (Gly-Pen-Gly-Arg-Gly-Asp-Ser-Pro-Cys-Ala [cyclical])

Antineoplastic agents:
1. Alkylating agents, such as nitrogen mustards (chlorambucil, cyclophosphamide, mechlorethamine, melphalan), ethyleneamine derivatives (thiotepa), alkyl sulfonates (busulfan), nitrosoureas (carmustine, lomustine), triazenes (dacarbasine)

2. Antimetabolites, such as folic acid analogues (methotrexate), pyrimidine analogues (cytarabine, floxuridine, fluorouracil), purine analogues (mercaptopurine, thioguanine)

3. Natural Products, such as vinca alkaloids (vinblastine, vincristine, paclitaxel), podophyllotoxin and its derivatives (etoposide); antibiotics (bleomycin, dactinomycin, doxorubicin, daunomycin, methramycin, mitomycin)

4. Hormones, such as adrenal corticosteroids (prednisone), estrogens (chlorotrianisene, conjugated estrogens, diethylstilbestrol, diethylstilbestrol diphosphate, ethinyl estradiol), androgens (calusterone, dromostanolone propionate, fluoxymesterone, testolactone, testosterone propionate, testosterone enanthate), progestine (hydroxyprogesterone, medroxyprogesterone, megestrol), antiestorgen (tamoxifen)

5. Enzymes, such as asparaginase

6. Miscellaneous agents, such as substituted urea (hydroxyurea), methyl hydrazine derivative (procarbazine), adrenocortical suppressant (mitotane), heavy metal complex (cisplatin, carboplatin)

The foregoing is offered primarily for purposes of illustration. It will be readily apparent to those skilled in the art that the materials, proportions, methods of preparation and formulation and other parameters of the various systems described herein may be further modified or substituted in various ways without departing from the spirit and scope of the invention.

What is claimed is:

1. A method for the preparation of an aqueous suspension of monodisperse non-crosslinked particles of albumin having a size range of from about 50 to about 5000 nanometers in diameter and stable against resolubilization, said method comprising:

(a) forming an aqueous solution containing as solutes:
      (i) albumin, and
      (ii) polyethylene glycol; and (b) treating said aqueous solution with a lower alkyl alcohol in an amount sufficient to cause said aqueous solution to become turbid.

2. A method in accordance with claim 1 in which said solutes are used at a concentration such that said particles comprise from about 1.0 to about 150 g per liter of said suspension.

3. A method in accordance with claim 1 in which said alcohol is a member selected from the group consisting of methanol, ethanol, n-propanol, isopropanol and n-butanol.

4. A method in accordance with claim 1 in which said alcohol is a member selected from the group consisting of ethanol and n-butanol.

5. A method in accordance with claim 1 in which step (b) comprises adding said lower alkyl alcohol in an amount such that said lower alkyl alcohol constitutes from about 10% to about 80% by volume of said suspension.

6. A method for the preparation of an aqueous suspension of monodisperse non-crosslinked particles of albumin having a size range of from about 50 to about 5000 nanometers in diameter and stable against resolubilization, said method comprising:

(a) treating an aqueous solution of albumin with a lower alkyl alcohol in an amount sufficient to cause said aqueous solution to become turbid; and (b) adding a polyethylene glycol to said turbid solution in a resolubilization suppressing amount.

7. A method in accordance with claim 6 in which said alcohol is a member selected from the group consisting of methanol, ethanol, n-propanol, isopropanol and n-butanol.

8. A method in accordance with claim 6 in which said alcohol is a member selected from the group consisting of ethanol and n-butanol.

9. A method in accordance with claim 6 in which step (a) comprises adding said lower alkyl alcohol in an amount such that said lower alkyl alcohol constitutes from about 10% to about 80% by volume of said suspension.

10. A method in accordance with claim 6 in which the polyethylene glycol is at a concentration of at least about 0.1 g per liter of said aqueous solution.

11. A method for the preparation of an aqueous suspension of monodisperse non-crosslinked particles of albumin having a size range of from about 50 to about 5000 nanometers in diameter, said particles being stable against resolubilization and containing fibrinogen adhered to the particle surface, said method comprising:

(a) forming an aqueous solution containing as solutes:
  (i) albumin, and
  (ii) polyethylene glycol in a resolubilization suppressing amount;

(b) treating said aqueous solution with a lower alkyl alcohol in an amount sufficient to cause said aqueous solution to become turbid; and contacting said particles with fibrinogen.

* * * * *